US010341866B1

(12) United States Patent
Spencer et al.

(10) Patent No.: US 10,341,866 B1
(45) Date of Patent: Jul. 2, 2019

(54) SECURE COMMUNICATION ARCHITECTURE FOR MEDICAL DEVICES

(71) Applicant: Bigfoot Biomedical, Inc., Milpitas, CA (US)

(72) Inventors: Gil Spencer, Incline Village, NV (US); Kevin S. Lee, Milpitas, CA (US); Cameron Hinkel, San Jose, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 0 days.

(21) Appl. No.: 15/959,450

(22) Filed: Apr. 23, 2018

Related U.S. Application Data

(63) Continuation of application No. 15/431,452, filed on Feb. 13, 2017, now Pat. No. 9,980,140.

(Continued)

(51) Int. Cl.
*G06K 5/00* (2006.01)
*H04W 12/06* (2009.01)
(Continued)

(52) U.S. Cl.
CPC ............ *H04W 12/06* (2013.01); *A61M 5/172* (2013.01); *G06F 21/44* (2013.01); *G06F 21/602* (2013.01);
(Continued)

(58) Field of Classification Search
CPC ........ A61B 5/14532; A61B 2560/0271; A61B 5/1118; A61B 5/4839; G06F 19/3418;
(Continued)

(56) References Cited

U.S. PATENT DOCUMENTS 8,401,194 B2 3/2013 Nierzwick et al.
8,472,630 B2 6/2013 Konrad et al.
(Continued)

OTHER PUBLICATIONS

Apple, "Local and Push Notification Programming Guide", Aug. 9, 2011, retrieved from the internet Aug. 16, 2017, https://web.archive.org/web/20130430092753/http://developer.apple.com/library/IOS/#/web/20130429070049/http://developer.apple.com:80/library/ios/DOCUMENTATION/NetworkingInternet/Conceptual/RemoteNotificationsPG/Chapters/ApplePushService.html>, 56 pages.

(Continued)

*Primary Examiner* — Thien M Le
(74) *Attorney, Agent, or Firm* — Brake Hughes Bellermann LLP

(57) ABSTRACT

In one implementation, a computer-implemented method of establishing a secure wireless communication connection between an insulin pump device and a mobile computing device includes receiving, at a mobile computing device, a device identifier for the insulin pump device; obtaining, by the mobile computing device, device information for the insulin pump device from a remote server system using the device identifier; establishing, by the mobile computing device, a secure wireless connection with the insulin pump device using, at least in part, the device information; authenticating, by the mobile computing device, the insulin pump device based on asymmetric key verification using the public key for the insulin pump; and securely communicating, by the mobile computing device and in response to authenticating the insulin pump device, information with the insulin pump device.

20 Claims, 19 Drawing Sheets

Related U.S. Application Data

(60) Provisional application No. 62/294,279, filed on Feb. 11, 2016.

(51) Int. Cl.
| | | |
|---|---|---|
| *A61M 5/172* | (2006.01) | |
| *G06K 7/10* | (2006.01) | |
| *G06K 19/06* | (2006.01) | |
| *G06K 7/14* | (2006.01) | |
| *H04L 29/06* | (2006.01) | |
| *G06F 21/44* | (2013.01) | |
| *H04L 9/06* | (2006.01) | |
| *G06F 21/60* | (2013.01) | |
| *H04L 9/32* | (2006.01) | |
| *H04W 12/02* | (2009.01) | |

(52) U.S. Cl.
CPC ....... *G06K 7/10722* (2013.01); *G06K 7/1413* (2013.01); *G06K 19/06028* (2013.01); *H04L 9/0631* (2013.01); *H04L 9/0637* (2013.01); *H04L 9/3236* (2013.01); *H04L 9/3271* (2013.01); *H04L 63/0435* (2013.01); *H04L 63/18* (2013.01); *H04W 12/02* (2013.01); *A61M 2205/50* (2013.01); *H04L 2209/80* (2013.01); *H04L 2209/88* (2013.01)

(58) Field of Classification Search
CPC ............. G06F 19/3406; G06F 19/3456; G06F 17/30876; H04L 2209/88; H04L 9/0822; H04L 9/0825

See application file for complete search history.

(56) References Cited

U.S. PATENT DOCUMENTS

| | | | |
|---|---|---|---|
| 8,533,475 | B2 | 9/2013 | Frikart et al. |
| 8,687,811 | B2 | 4/2014 | Nierzwick et al. |
| 2007/0016449 | A1* | 1/2007 | Cohen ................. G06F 19/3456 705/3 |
| 2008/0046581 | A1 | 2/2008 | Molina et al. |
| 2008/0312512 | A1 | 12/2008 | Brukalo |
| 2009/0250512 | A1 | 10/2009 | Deck et al. |
| 2010/0281252 | A1 | 11/2010 | Steeves et al. |
| 2011/0081860 | A1 | 4/2011 | Brown et al. |
| 2012/0266251 | A1 | 10/2012 | Birtwhistle et al. |
| 2013/0179685 | A1 | 6/2013 | Weinstein et al. |
| 2013/0238140 | A1* | 9/2013 | Malchiondo ........ H04L 12/2807 700/276 |
| 2013/0317753 | A1* | 11/2013 | Kamen ................ G06F 19/3418 702/19 |
| 2014/0184422 | A1* | 7/2014 | Mensinger ........... A61B 5/0004 340/870.02 |
| 2014/0188398 | A1* | 7/2014 | Cohen ................. A61B 5/14532 702/19 |
| 2014/0281547 | A1 | 9/2014 | Modzelewski et al. |
| 2015/0207626 | A1* | 7/2015 | Neftel .................... G08C 17/02 713/168 |
| 2015/0223433 | A1* | 8/2015 | Navawongse ....... A01K 29/005 119/421 |
| 2017/0293732 | A1 | 10/2017 | Cohen |
| 2017/0311903 | A1* | 11/2017 | Davis .................... G16H 50/20 |

OTHER PUBLICATIONS

Goggle, "Google Cloud Messaging: Overview", Nov. 23, 2016, retrieved from the internet Aug. 16, 2017, https://developers.google.com/cloud-messaging/gcm>, 5 pages.

* cited by examiner

SECURE COMMUNICATION ARCHITECTURE FOR MEDICAL DEVICES

CROSS-REFERENCE TO RELATED APPLICATIONS

This application claims priority to, and the benefit of, U.S. patent application Ser. No. 15/431,452, filed Feb. 13, 2017, entitled SECURE COMMUNICATION ARCHITECTURE FOR MEDICAL DEVICES, which claims priority to, and the benefit of, U.S. Provisional Application Ser. No. 62/294,279, filed Feb. 11, 2016, entitled SECURE COMMUNICATION ARCHITECTURE FOR MEDICAL DEVICES, both of which are hereby incorporated by reference in their entireties.

TECHNICAL FIELD

This document generally describes technology related to security and secure communication between medical devices, such as insulin pump devices, and computing devices, such as computer systems and/or smartphones.

BACKGROUND

A number of different technologies have been developed to improve computer security and secure communication between medical devices and computing devices. For example, public key encryption has been used to provide secure authentication and to establish symmetric keys that can be used to encrypt communication between computing devices across a potentially unsecure communication network, such as a public network like the internet. Public key encryption involves each computing device generating a public encryption key and a corresponding private encryption key. The public encryption key can be published by a computing device and used by other computing devices to establish a symmetric key that the computing device can use to encrypt communication between the devices. For example, values that are used to create symmetric keys can be transmitted between computing devices using public and private keys for each of the devices. Symmetric keys can subsequently be used to encrypt communication that is transmitted between computing devices so that the contents of the communication are not readily viewable to parties/entities who are not privy to the symmetric keys that are being used, such as to a man in the middle of the communication (e.g., node along a transmission path for the communication).

SUMMARY

This document generally describes computing architectures to provide secure connections and communication between medical devices (e.g., insulin delivery devices, drug delivery devices, health monitoring devices) and computing devices, such as computer systems, mobile computing devices (e.g., smartphones, tablet computing devices). In particular, such computing architectures (and associated techniques, devices, and systems) can be used to provide secure connections and communication when using a medical device with a limited user interface that is not capable of readily outputting information or receiving user input, such as a code, that can be used to configure secure connections and communication with computing devices. For example, a drug delivery device, such as an insulin pump, may have a limited user interface that includes one or more lights (e.g., LED lights) to provide status information for the device, but may not include a display that would be capable of readily outputting information or a user interface through which a user could provide input to configure secure connections and communication with other devices, such as smartphones.

A variety of techniques and architectures can be used to provide secure connections and communication between medical devices and other computing devices, including between devices with limited user interfaces as well as devices with more comprehensive user interfaces (e.g., touch-based user interfaces, speech-based user interfaces). For example, a computer system (e.g., server system) can be programmed to securely store and distribute information to authenticated and verified users/devices. For instance, a mobile computing device can obtain a unique identifier for a medical device, such as through optical scanning (e.g., barcode/QR code scanner) and/or radio frequency detection (e.g., RFID), and transmit the unique identifier to a server system. The server system can authenticate the mobile computing device and/or its user and, once authenticated, can provide the mobile computing device with the medical device's information (e.g., peripheral device public encryption key, peripheral device authentication certificate) based on the unique identifier for the medical device. The mobile computing device can establish a secure connection with the medical device using the medical device's information, for example, as a secret shared between the mobile computing device and the medical device (which can already store its own medical device information).

For example, when securely pairing a medical device with a computing device via a BLUETOOTH connection, one of the devices can output a code (e.g., PIN code) that will then be input through a user interface on the other device to provide a shared secret between the devices. This shared secret can be used to compute values that are used to authenticate the two devices with each other during a BLUETOOTH challenge/response process. In the example described above, the mobile computing device can use some of the medical device's information obtained from a server system (e.g., application services system, web services system), such as the medical device's public encryption key (which is also stored by the medical device), as a shared secret to establish a secure BLUETOOTH connection between the devices without the medical device having to either output a code or provide an interface to input a code.

With a secure and authenticated connection established between a mobile computing device and a medical device, the mobile computing device can further use the medical device information to validate that the mobile computing device is connected to the correct medical device. For example, the mobile computing device can use the medical device's authentication certification, which was provided by the server system, to validate the identity of the medical device.

Likewise, the medical device can also validate the mobile computing device to ensure that it is connected with a valid/authorized mobile computing device. To do this, the medical device can communicate with the server system to obtain mobile computing device information, such as an authorization certificate and/or other identifying information from the server system. The communication between the medical device and the server system can use the secure connection with and can be relayed by the mobile computing device. The medical device and the server system can use pass-through encryption techniques so that there is end to end encryption between the medical device and the server system, which restricts the mobile computing device (and any other nodes in the communication path) from reading the information that is transmitted between the medical device and the server system. Once the medical device has the mobile computing device information, the medical device can verify whether it is connected to a valid/authentic mobile computing device (and/or a valid/authentic application that is running on the mobile computing device).

In one implementation, a computer-implemented method of establishing a secure wireless communication connection between an insulin pump device and a mobile computing device, the method includes receiving, at a mobile computing device, a device identifier for the insulin pump device, wherein the insulin pump device includes an insulin reservoir to store insulin to be administered to a user, a pump assembly to delivery insulin from insulin reservoir to the user, and a controller to control operation of the pump assembly according, at least in part, to commands provided to the insulin pump by the mobile computing device; obtaining, by the mobile computing device, device information for the insulin pump device from a remote server system using the device identifier, wherein the device information includes, at least, a public key for the insulin pump device, wherein the insulin pump device has a corresponding private key that is stored locally by the insulin pump device; establishing, by the mobile computing device, a secure wireless connection with the insulin pump device using, at least in part, the device information; authenticating, by the mobile computing device, the insulin pump device based on asymmetric key verification using the public key for the insulin pump; and securely communicating, by the mobile computing device and in response to authenticating the insulin pump device, information with the insulin pump device.

In another implementation, a computer-implemented method of establishing a secure wireless communication connection between an medical device and a mobile computing device, the method including receiving, at a mobile computing device, a device identifier for the medical device; obtaining, by the mobile computing device, device information for the medical device from a remote server system using the device identifier, wherein the device information includes, at least, a public key for the medical device, wherein the medical device has a corresponding private key that is stored locally by the medical device; establishing, by the mobile computing device, a secure wireless connection with the medical device using, at least in part, the device information; authenticating, by the mobile computing device, the medical device based on the device information, wherein the authenticating includes: transmitting, by the mobile computing device, a challenge message to the medical device; receiving, at the mobile computing device and in response to the challenge message, a signed message from the medical device, wherein the signed message includes a message and an encrypted hash appended to the message; decrypting, by the mobile computing device, the encrypted hash with the public key for the medical device to generate a decrypted hash; independently generating, by the mobile computing device, a hash of the message; comparing, by the mobile computing device, the decrypted hash with the independently generated hash of the message; and determining, by the mobile computing device, that the medical device is authentic based on the decrypted hash matching the independently generated hash; and securely communicating, by the mobile computing device and in response to authenticating the medical device, information with the medical device.

In another implementation, a computer-implemented method includes receiving, at a mobile computing device, a device identifier for a peripheral device that is currently communicatively disconnected from the mobile computing device; encrypting, by the mobile computing device and using one or more encryption keys that are associated with a computer system, the device identifier for transmission; transmitting, by the mobile computing device, the encrypted device identifier to the computer system over a first encrypted communication channel; receiving, at the mobile computing device, information for the peripheral device, wherein the information includes, at least, a public encryption key for the peripheral device; establishing, by the mobile computing device, a second encrypted communication channel to securely communicate with the peripheral device, wherein establishing the second encrypted communication channel includes: transmitting, by the mobile computing device and to the peripheral computing device, a first challenge that includes a first value; determining, by the mobile computing device, a correct response value for the challenge based on (i) the first value and (ii) the public encryption key for the peripheral device; receiving, at the mobile computing device and from the peripheral computing device, a peripheral device response value; comparing, by the mobile computing device, the correct response value with the peripheral device response value; authenticating, by the mobile computing device, the peripheral device based on the correct response value matching the peripheral response value; receiving, at the mobile computing device and from the peripheral device, a second challenge that includes a second value; determining, by the mobile computing device, a mobile device response based on (i) the second value and (ii) the public encryption key for the peripheral device; transmitting, by the mobile computing device, the mobile device response to the peripheral device; and receiving, at the mobile computing device and from the peripheral device, confirmation that the mobile computing device has been authenticated with the peripheral device; and communicating, by the mobile computing device and in response to authenticating the peripheral device and receiving the confirmation, with the peripheral device over the second encrypted communication channel.

Certain implementations may provide one or more advantages. For example, medical devices are special types of devices that often provide essential medical therapies to users (e.g., insulin delivery, pace making therapy) which, if administered correctly, can provide life-saving/health improving benefits, but if not administered correctly, can be potentially life-threatening and dangerous to users. Therapies that are provided by medical devices can benefit from and be improved by offloading computationally intensive processes, such as constructing user-specific dosing models from user dosing data (e.g., medicine dosages delivered, user response to dosages) and using user-specific dosing models to determine when and in what amounts to deliver medicines to a user. However, secure and authenticated communication between medical devices and other computing devices can be needed in order to offload such computationally intensive processes in a way that will prevent malicious or unauthenticated connections with the medical devices that could put users at risk (e.g., risks from malicious control commands being sent to the medical device that could potentially damage a user's health). Accordingly, secure communication and connections between medical devices and other computing devices can allow for medical devices to provide better therapies while at the same time to prevent potentially damaging or malicious connections with the medical devices.

In another example, medical devices can be securely paired and connected to a computer system without the need for a robust user interface (e.g., display, touchscreen, speaker). For instance, medical devices and drug delivery devices can be securely paired and connected to a computer system without the devices needing a display to output a code or an input mechanism to receive a code. This can reduce the cost of producing such devices both in terms of materials (e.g., display, touchscreen, keyboard, speaker, and other user interface components not needed) and in terms of device complexity (e.g., user interface features do not need to be coded, tested, and supported).

In a further example, with these techniques, devices with limited user interfaces can still receive the benefits of having secure connections with other computing devices/computer systems, which can have greater processing resources to offload processing operations from the medical devices. For example, a medical device or drug delivery device may tailor the functions that it performs (e.g., insulin delivery, cardiac pacing) for the device's specific user based on data for the user that the device acquires over time (e.g., insulin delivery device may customize insulin delivery for the device's user based on insulin dosages and the corresponding effects to the user's blood glucose levels). However, such customization may be computationally intensive (e.g., use machine learning algorithms) and may need more computing resources (e.g., processor cycles, memory, storage) than a medical device has available. By establishing secure connections with other devices, which can perform the more computationally intensive operations and then provide the actionable output (e.g., insulin dosing model), the medical device can implement more robust features without needing to have robust computing resources. This can improve the performance of medical devices, which can provide enhanced features without incurring the associated processing burden and while conserving power consumption (e.g., reducing use of computing resources) and improving battery performance.

In another example, controllers and/or mobile computing devices can be authenticated so that they only communicate with an insulin pump that was authorized for particular user/patient accounts maintained/managed by a computer system (e.g., web service). With this framework, data can also be validated as being received from registered users/ patients for a medical device (e.g., insulin delivery device) and not from other, unauthorized users. Medical devices can also validate that the stream of commands they receive are only from authorized mobile computing devices/controllers, and/or only from valid computer systems (e.g., web service providers), and not from a rogue attacker. Commands can also be validated as only being for particular users/patients and their associated medical devices. Data and/or commands that are transmitted between devices/systems (either way) can also be verified as having not been tampered with or otherwise modified in transit.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This document generally describes computing architectures, systems, devices, and techniques for providing secure connections and communication between medical devices (e.g., drug delivery devices, health monitoring devices) and computing devices/systems, such as remote server systems (e.g., cloud-based computer systems), mobile computing devices (e.g., smartphones, tablet computing devices).

Figure 1:
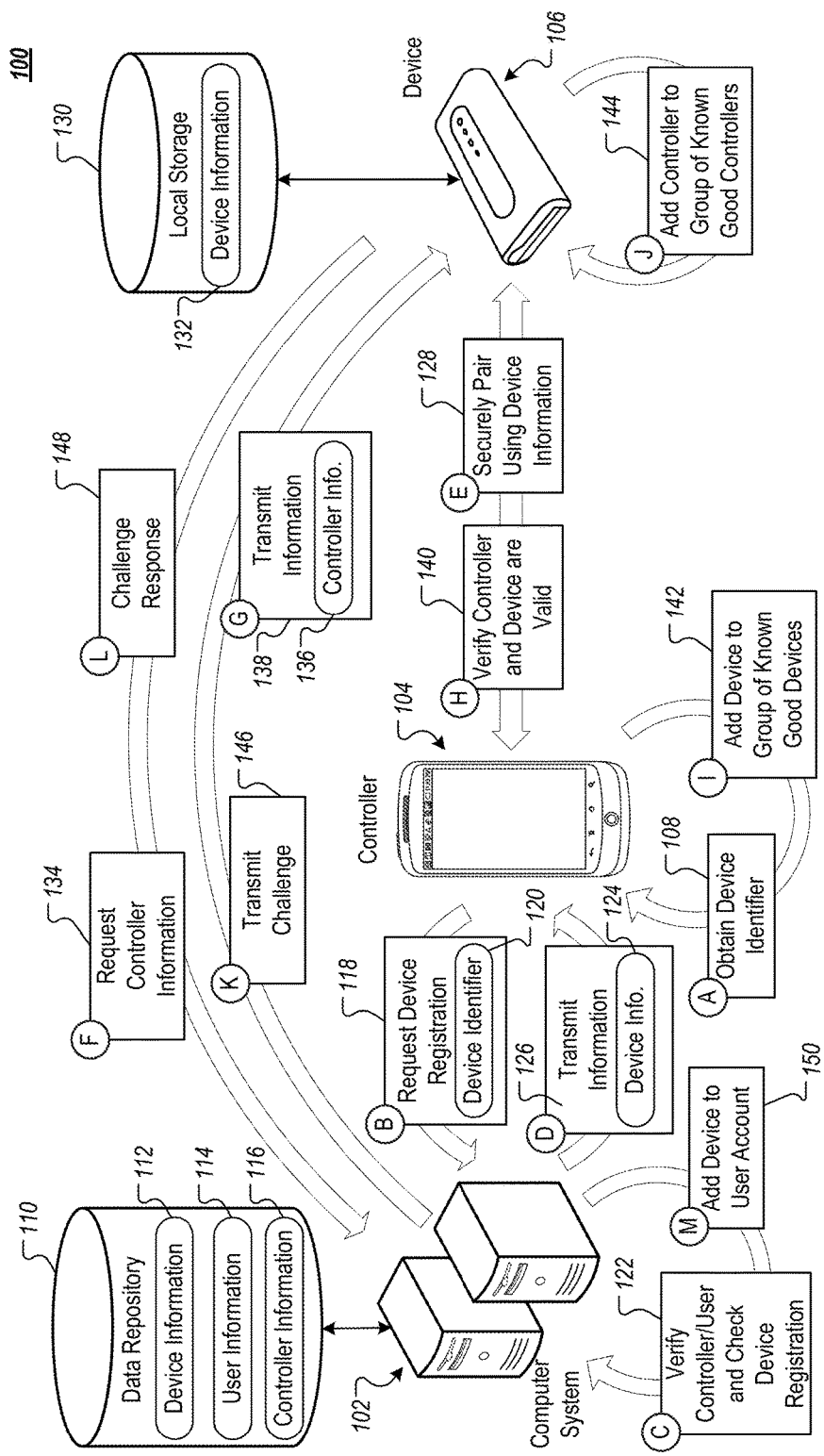
FIG. 1 is a conceptual diagram of an example system to provide secure connections and communication between an example computer system, an example controller, and an example device.

FIG. 1 is a conceptual diagram of an example system 100 to provide secure connections and communication between an example computer system 102, an example controller 104, and an example device 106. The example computer system 102 can be any of a variety of appropriate systems that include one or more computing devices, such as web server systems and/or cloud-based computer systems. The example controller 104 can be any of a variety of appropriate computing device, such as a mobile computing device (e.g., smartphone, tablet computing device), desktop computer, laptop, and/or other appropriate computing devices. The device 106 can be any of a variety of appropriate peripheral devices that, at least in part, are programmed to be controlled by or otherwise communicate with the controller 104. For example, the device 106 can be a medical device (e.g., pacemaker, defibrillator), a drug delivery device (e.g., insulin pump, inhaler), a health monitoring device (e.g., fitness tracker, heat rate monitor, continuous glucose monitor (CGM)), and/or other appropriate peripheral devices (and/or group of devices, such as a group including an insulin delivery device and continuous glucose monitoring device).

In the depicted example, the system 100 can use connections and communication among the system 102, the controller 104, and the device 106 to provide features to a user, such as the device 104 delivering medicine to the user in appropriate dosages and at appropriate times based on user-specific dosing models determined and/or implemented by the computer system 102 and/or the controller 104. Information that is transmitted among the computer system 102, the controller 104, and the device 106 can be sensitive, private information (e.g., patient data, user-specific medicine dosing model) that is not suitable for open and unsecured transmission, such as through unencrypted communication over the internet.

Establishing secure and authenticated connections between the computer system 102, the controller 104, and the device 106 can present a number of technical hurdles. For example, the device 106 can have a limited user interface that does not include an output subsystem capable of readily outputting information, such as text or codes, or an input subsystem capable of readily receiving information, such as text or codes. For instance, the device 106 may simply have one or more lights (e.g., LEDs) to provide status information (e.g., whether the device is on/off, whether the device is connected to another device) and may have a motion sensor to detect movement or other use of the device 106. However, the device 106 may not have a display or a speaker to output information that is more complex than simple binary status information. Additionally (or alternatively), the device 106 may not have a touchscreen, microphone, keys/buttons, or other input mechanisms to receive input that is more complex than a simple movement of the device 106.

With a limited user interface, the device 106 may not be able to readily and securely share secrets with other devices, such as the controller 104, that are used to establish secure connections (e.g., secure BLUETOOTH connections, Wi-Fi Direct connections) that can be used for authentication among devices. For example, to establish a secure BLUETOOTH connection between a peripheral device and a mobile computing device, one of the devices can output a code that a user then enters into the other device—meaning that at least one of the devices needs a way to output the code (e.g., a display, an audio speaker) and the other device needs a way to input the code (e.g., touchscreen, keypad, microphone with speech-based interface). With a limited user interface, the device 106 may not have either a way to readily output a code or a way to input a code.

An example technique for establishing secure authenticated connections among the computer system 102, the controller 104, and the device 106 in the example system are described with regard to steps A-K. This example technique can be performed when the device 106 has a limited user interface, no user interface, a more robust user interface (e.g., touchscreen user interface, display and key/button based user interface, speech-based user interface), or any other appropriate user interface.

Before step A (108) is performed, the controller 104 may not have any information regarding the device 106. For example, the controller 104 may not have received any identifiers, keys, certificates, or other information specific to the device 106 that could be used to establish secure connections with the device 106. However, the computer system 102 can have previously received information 112 for the device 106 that is stored in a data repository 110 (e.g., databases, data server system, cloud-based storage system) that is accessible to the computer system 102. The information 112 can include a variety of details regarding the device 106, such as a unique identifier (e.g., serial number, assigned unique identifier), product information (e.g., model number, manufacture date, ship date, point of sale, firmware/operating system version, MAC address for the device 106), secure communication information (e.g., public encryption key for the device 106), authentication information (e.g., authentication certificate, other secret value), and/or other appropriate information that can be used to communicate with the device 106. The information 112 can be generated and populated into the data repository 110 from before sale/distribution of the device 106 (e.g., populated during a manufacturing/production process).

The data repository 110 can also include user information 114. The user information 114 can include information for users who are registered with the computer system 102, such as usernames, passwords, contact information (e.g., email, phone number, preferred method of contact), medical information (e.g., medical conditions, prescriptions, doctor), user data (e.g., medical data, dosing data), user profiles/models (e.g., medication/dosing profiles that generated from the user data), associated devices (e.g., unique identifiers for devices that are registered for a user), associated controllers (e.g., unique identifiers for controllers that are registered for a user), and/or other appropriate information. The user information 114 can initially be stored in the data repository 110 when users register with the computer system 102, such as through a web browser or mobile app (e.g., mobile app installed on the controller 104). The user information can be updated overtime through secure communication with, for example, the controller 104 and/or the device 106. For instance, user medical data that may be updated on recurring basis (e.g., updated every 10 minutes, every 30 minutes, every hour, every 12 hours, every day, every week).

The data repository 110 can also include controller information 116, which can include information a variety of details regarding the controller 104. For example, the controller information 116 can include unique identifiers (e.g., serial number, assigned unique identifier), product information (e.g., model number, firmware/operating system version, MAC address for the controller 104, hardware information such as CPU model/specs, RAM, internal storage device capacity), secure communication information (e.g., public encryption key for the controller 104), authentication information (e.g., authentication certificate, other secret value), application information (e.g., information identifying the installed application(s) on the device, unique identifiers for the application(s)), and/or other appropriate information that can be used to communicate with or otherwise identify the controller 104. The controller information 116 can be initially be stored in the data repository 110 when the controller 104 initially registers with the computer system 102, such as when a user installs an application on the controller 104 that is hosted/supported by the computer system 102, when a user associates the controller 104 with his/her account, and/or other registration/initialization activities, such as a third party (e.g., nurse, physician) initializing the controller 104 (and/or the device 106) on behalf a user/patient.

When step A (108) is performed, a user and the controller 104 can already be registered with the computer system 102 and can be associated with each other in the data repository 110. The example technique depicted in steps A-K can involve registering and authenticating the device 106 with the controller 104 and the computer system 102. As depicted in step A (108), the controller 104 can obtain an identifier for the device 106. The controller 104 can do this in any of a variety of appropriate ways. For example, device 106 can have a scannable code (e.g., barcode, QR code) affixed to, imprinted on, or otherwise visible on one or more of the surfaces of the device 106 (or in associated materials, such as packaging for the device 106) that encodes the identifier for the device 106. For instance, the controller 104 can have a digital camera and an application (e.g., mobile app such as REDLASER) that is programmed to capture one or more images (or videos) of the code and to detect the identifier from the images using image processing techniques (e.g., optical character recognition, object recognition, edge detection techniques). In another example, the device 106 can have one or more RFID tags that encode the identifier that are detectable by the controller 104, which can have one or more embedded RFID readers, such as a near field communication (NFC) chip. In a further example, the controller 104 can provide a user interface through which a user can input a unique identifier for the device 106, which may be identified on the device 106 or other associated materials (e.g., product package).

Once the controller 104 has obtained the device identifier, the controller 104 can transmit a request to register the device to the computer system 102, as indicated by step B (118). The request can include the device identifier 120 and can be transmitted with information that uniquely identifies the controller 104 (e.g., unique controller identifier), one or more applications that are running on the controller (e.g., unique app identifier), and/or an identifier for an associated user (e.g., user account identifier). The request can be securely transmitted to the computer system 102, for example, by encrypting the contents of the packets that are transmitted to the computer system 102 using one or more encryption techniques.

In response to receiving the request to register the device 106 with the controller 104 and its associated user, the computer system 102 can verify the controller and user (e.g., verify username and password, verify authentication certificate for the controller 104 and/or its application), and can check whether the device is already registered, as indicated by step C (122). For example, the computer system 102 can be programmed to restrict registration of each device to a single user account. However, the computer system 102 may permit each user account to register multiple devices and/or multiple controllers. In response to determining that the requested registration can proceed, the computer system 102 can retrieve information for the device 106 from the repository 110, such as a public key for the device 106 and an authentication certificate for the device 106, which were previously provisioned on the device 106 and stored in the repository 110. The computer system 102 can transmit this information 124 to the controller 104, as indicated by step D (126).

The controller 104 can use the information 124 for the device 106 to securely pair the controller 104 with the device 106, as indicated by step E (128). For example, the device 106 can have local storage 130 that already includes a corresponding copy of the device information 132, which can include all of the information 124 that is transmitted to the controller 104 as well as additional information for the device 106. For instance, the information 124 that is transmitted to the controller 104 by the computer system 102 may only include a public encryption key for the device. However, the information 132 that is stored locally on the device 106 can include the public encryption key as well as a corresponding private encryption key for the device 106.

One or more portions of the information that is common to both the information 124 received by the controller 104 and the information 132 stored locally by the device 106 can be used as a shared secret to securely pair the controller 104 and the device 106, such as through a BLUETOOTH pairing procedure and/or through a Wi-Fi Direct pairing procedure. For example, the device 106 and the controller 104 can use the public encryption key (or portions thereof) for the device 106 as the shared secret that the controller 104 and the device 106 use to generate values that they transmit to each other and verify during a pairing challenge and response process (ensuring that only the controller 104 can connect to the device 106). Other common information could additionally or alternatively be used as the shared secret, such as an authentication certificate (or portions thereof) for the device 106, a randomly generated value for the device 106 that is stored in the repository 110, and/or other information. The controller 104 and the device 106 may avoid using information that is more accessible as the shared secret, such as the identifier 120 for the device 106, which may be visibly accessible on the housing for the device 106 and/or through radio transmissions (e.g., RFID tag).

By having common, shared information that is generally not public (e.g., the device information 124 is not shared publicly by the computer system 102 or the device 106), the device 106 is able to be paired with the controller 104 in a secure manner without the device 106 needing to have the capacity to either output a code or to receive a code as input. Accordingly, the device 106 can be securely paired with the controller 104 regardless of whether the device 106 has a limited user interface or a more robust user interface. Similarly, the device 106 can be securely paired with the controller 104 without needing manual inputs from a user one the device 106 or the controller 104.

In some cases, the secure pairing can include authentication of the device 106 using a public key for the device 106 by signing and verifying messages between the device 106 and the controller 104. For example, the device 106 can have a private key that corresponds to the public key for the device 106, which has been provided to the controller 104 as part of the device information 124. The device 106 can generate a message that includes information that is known to both the device 106 and the controller 104, such as the device identifier 120 for the device 106. The device 106 can further sign the message using a hash of the message that is encrypted with the private key for the device 106 and appended to the end of the message. The device 106 can transmit the signed message to the controller 104, which can use the public key for the device 106 to decrypt the hash appended to the end of the message, can hash the message, and can compare the decrypted hash with the hash generated by the controller 104 to authenticate the device 106. If the hashes match (the decrypted hash and the controller 104 generated hash of the message), then the controller 104 can determine that the device 106 is authentic (is the device it purports to be). The controller 104 can be verified in a similar manner by device 106, for example, using a public key for the controller 104.

Having been paired so that they can securely communicate with each other (e.g., over a secure BLUETOOTH connection, Wi-Fi Direct connection), the controller 104 and the device 106 can then seek to verify that they are communicating with devices that are authorized and authenticated with the computer system 102. Such verification can be performed in any of a variety of ways, and can include each device verifying that the other device is able to provide information, such as a certificate or information computed based on a certificate, that matches information received from the computer system 102 for the device. Each of the controller 104 and the device 106 can independently obtain information about the other device from the computer system 102. In the case of the controller 104 performing verification of the device 106, the information used to verify the device 106 can be provided to the controller 104 by the computer system 102 as part of the device information 124.

In the case of the device 106 performing verification of the controller 104, the device 106 may need to obtain information about the controller 104 from the computer system 102 after the device 106 has been paired to the controller 104, as indicated by step F (134). The device 106 can do this in any of a variety of ways. For example, once paired, the controller 104 may provide pass-through communication between the device 106 and the computer system 102. Such pass-through communication can include end-to-end encryption from the device 106 to the computer system 102 so that intermediary devices along the communication path, such as the controller 104, are not able to detect the contents of the transmission. Such pass-through encryption between the device 106 and the controller 102 can be performed by using public and private encryption keys for the computer system 102 and the device 106. In another example, if the device 106 has another network connection (other than its pairing with the controller 104), such as an internet connection through a wireless network (e.g., Wi-Fi network), the device 106 can communicate with the computer system 102 without having to pass-through the controller 104.

In response to receiving the request for controller information, the computer system 102 can retrieve appropriate controller information 136 from the repository 110 and can transmit it to the device 106, as indicated by step G (138). The controller information 136 can include information that can validate/verify the authenticity of the controller 104, such as an authentication certificate for the controller 104, a secret value maintained by the computer system 102 for the controller 104, and/or some other information that can be used to validate/authenticate the controller 104. By either transmitting the controller information 136 using pass-through encryption at the controller 104 or using a communication channel that does not include the controller 104, the device 106 can obtain the controller information 136 independent of any information that the controller 104 will provide to verify itself, which can ensure the integrity of the verification process.

Using the device information 124 and the controller information 136, the device 106 and the controller 104 can verify each other, as indicated by step H (140). For example, the controller 104 can verify the device 106 by obtaining verifying information (e.g., authentication certificate) from the device 106 and determining whether the verifying information matches corresponding portions of the device information 124 that was received from the computer system 102. For instance, the controller 104 can determine whether an authentication certificate received from the device 106 matches the certificate received from the computer system 102 for the device 106. If there is a match, then the device 106 can be verified with the controller 104. If there is not a match, then the controller 104 can report the mismatch to the computer system 102 and/or can cancel the pairing with the device 106. A mismatch may indicate that the device 106 is an imposter device (not the same device registered with the system 102) that is not to be trusted and used with the controller 104.

Once the controller 104 has verified the device 106, the controller 104 can add the device 106 to a group of known good (verified, trusted) devices that are maintained locally by the controller 104, as indicated by step I (142). For example, the controller 104 can maintain a list of devices that are verified so that the verification process does not have to be repeated each time the controller 104 and the device 106 are paired with each other. The information stored on such a list may expire after a period of time (e.g., once a month, once a quarter, once a year) and the verification process may be repeated periodically so as to ensure that another device is not imitating the device 106.

Similarly, in another example, the device 106 can verify the controller 104 by obtaining verifying information (e.g., authentication certificate) from the controller 104 and determining whether the verifying information matches corresponding portions of the controller information 136 that was received from the computer system 102. For instance, the device 106 can determine whether an authentication certificate received from the controller 104 matches the certificate received from the computer system 102 for the controller 104. If there is a match, then the controller 104 can be verified with the device 106. If there is not a match, then the device 106 can report the mismatch to the computer system 102 and/or can cancel the pairing with the controller 104. A mismatch may indicate that the controller 104 is an imposter device (not the same device and/or application registered with the system 102) that is not to be trusted and used with the device 106. Verification of the device 106 by the controller 104 can be performed at the same time or at a different time than verification of the controller 104 by the device 106.

Once the device 106 has verified the controller 104, the device 106 can add the controller 104 to a group of known good (verified, trusted) controllers that are maintained locally by the device 106, as indicated by step J (144). For example, the device 106 can maintain a list in the local storage 130 of controllers and/or other computing devices that have been verified as being authentic with the computer system 102, and can use such a list so that the verification process does not need to be repeated, for example, each time the device 106 is paired with the controller 104.

Although not depicted, the controller 104 and the device 106 can additionally/alternatively transmit verification information that is received from the device 106, such as retransmitting certificates that the controller 104 and/or the device receive from each other as part of the verification process, and/or transmitting confirmation that the controller 104 and/or device 106 have verified each other (e.g., transmit confirmation that information provided by the device 106 matches the device information 124 provided by the computer system 102). The computer system 102 can use this information to verify and/or confirm verification of the controller 104 and/or the device 106.

In addition to the controller 104 and the device 106 verifying each other, the computer system 102 can directly challenge and verify the device 106, which can provide redundant verification of the device 106. For example, the computer system 102 can transmit a challenge to the device 106, as indicated by step K (146). For instance, the computer system 102 can challenge the device 106 to provide a shared secret between the computer system 102 and the device 106 (e.g., shared secret that is stored in the data repository 110 for the computer system 102 and in the local storage 130 for the device 106). The shared secret can be different from the shared secret that is provided to and used by the controller 104 to verify the device 106. The communication between the computer system 102 and the device 106 can include a pass-through encryption communication channel that passes through (relayed by) the controller 104.

In response to receiving the challenge, the device 106 can determine an appropriate value, such as selecting an appropriate shared secret to retransmit and/or computing a value from such a shared secret, and can transmit it as a challenge response to the computer system 102, as indicated by step L (148). For example, the challenge response can include a certificate, another shared secret, and/or a value determined by the computing device 106 from one or more shared secrets. The computer system 102 can receive the challenge response and use it to determine whether the device 106 is valid/authentic. For example, the computer system 102 can determine whether the received value matches a value that is stored in the data repository 110 as part of the device information 112 and/or can determine whether the received value matches a corresponding value that the computer system 102 determines in parallel from a shared secret.

In response to determining that the controller 104 and/or the device 106 are valid, the computer system 102 can register the device 106 with an account for the user associated with the controller 104, as indicated by step M (150). The computer system 102 may require one or more of the following in order to register the device 106 with the user's account: validation of the device 106 by the controller 104, validation of the controller 104 by the device 106, validation of the device 106 by the computer system 102, validation of the controller 104 and/or applications that are running on the controller 104 by the computer system 102, and/or validation of the user account associated with the controller 104 by the computer system 102. Once appropriate requirements have been met, the device 106 can be registered with the user account, such as adding an identifier for the user account to the device information 112 and/or adding a device identifier to the user information 114 and/or controller information 116.

The computer system 102 can transmit confirmation of the device 106 being registered with the computer system 102 to the controller 104 and/or the device 106. The device 106 and the controller 104 can be programmed to restrict/prohibit transmitting private or confidential information (e.g., medical data, patient information, treatment models) with each other until the verification process (either directly or through referencing a list of verified devices/controller) and/or registration process has been completed. For example, in response to receiving confirmation that the device 106 has been registered, the controller 104 and the device 106 can transmit private and confidential information with each other.

Figure 2:
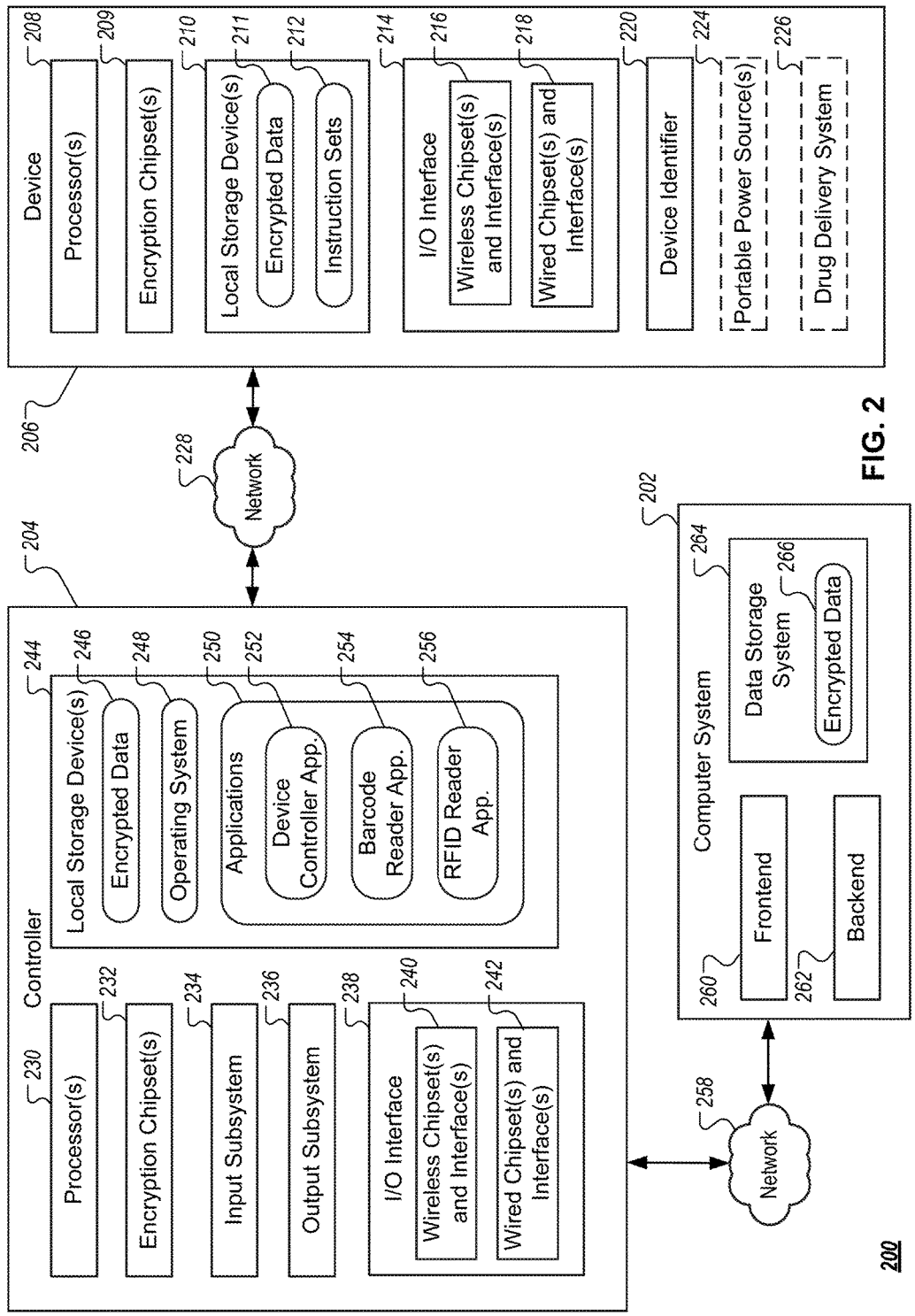
FIG. 2 is an example system for establishing secure communication channels between a computer system, a controller, and a device.

FIG. 2 is an example system 200 for establishing secure communication channels between a computer system 202, a controller 204, and a device 206. The computer system 202, the controller 204, and the device 206 can be similar to and can perform the same operations as the computer system 102, the controller 104, and the device 106, respectively, as described above with regard to FIG. 1.

The system 200 can be configured and programmed to implement one or more security policies in order to ensure secure communication and data among the system 202, the controller 204, and the device 206. For example, the system 200 can be programmed to: encrypt some or all data in transit between the system components 202-206, encrypt some or all data that is being stored at one or more of the system components 202-206, to restrict access to account information and associated account data to only authenticated and verified users, to restrict control of the device 206 to only authenticated and verified users through the controller 204 and/or other devices connected to the controller 204 or the computer system 202, to restrict access to private or confidential data (e.g., patient data, user information, information that can otherwise be attributed or identified as being associated with a user/patient) to only authorized and verified users, to restrict pairing with the device 206 to only controllers that are authenticated and authorized (e.g., controllers that have an authenticated and authorized mobile app installed), and/or to restrict firmware that is being installed, updated, and/or used on the device 206 to be signed and authenticated by the computer system 202. Other security policies for the system 200 are also possible.

In the example system 200, the device 206 includes one or more processors 208 (e.g., central processing unit (CPU), microprocessor), one or more encryptions chipsets 209 (e.g., crypto chip, cryptoprocessor, smartcards, trusted platform module (TPM), hardware security modules), and one or more local storage devices 210 (e.g., flash memory, solid state drive, hard drive, non-volatile memory, read only memory (ROM), erasable programmable read-only memory (EPROM)). The local storage devices 210 can include encrypted data 211 (e.g., data stored in an encrypted format) and one or more instruction sets 212 (e.g., firmware, operating system, applications). The one or more processors 208 can be programmed to perform operations according to the one or more instruction sets 212. The encryption chipsets 209 can be programmed to store encryption keys (e.g., asymmetric keys, symmetric keys), to authenticate other devices using the stored keys (e.g., sign messages with encrypted hashes, validate signed messages with encrypted hashes), to encrypt and decrypt the encrypted data 211 in the local storage devices 210, and/or to encrypt and decrypt information that is transmitted to the controller 204 and the computer system 202.

The processors 208 and the encryption chipsets 209 can be programmed to implement one or more of the security policies for the system 200, such as encrypting all data that is stored in the local storage device 210, require that the instruction sets 212 that are used by the device 206 be authenticated and signed by the computer system 202, and encrypting all data that is transmitted between the device 206 and other devices, such as the controller 204 and the computer system 202. For example, the processors 208 and the encryption chipsets 209 can be programmed to encrypt and to store the following as encrypted data 211: patient dosage parameters and models, patient data (e.g., sensor readings, medicine dosing log), keys for authentication and encryption, policies governing commands to which the device 206 responds, firmware and/or instructions that are executed by the device 206 (e.g., the instruction sets 212), and/or other appropriate information. Any of a variety of appropriate encryption techniques and algorithms can be used to encrypt data that is being stored in the local storage device 210, such as 128 bit, 192 bit, or 256 bit Advanced Encryption Standard (AES) in any of a variety of modes, such as cipher block chaining (CBC) mode, electronic codebook (ECB) mode, propagating cipher block chaining (PCBC) mode, cipher feedback (CFB) mode, Galois/Counter mode (GCM), and/or output feedback (OFB) mode.

The device 206 further includes an input/output (I/O) interface 214 that includes one or more of a wireless chipset and interfaces 216 (e.g., BLUETOOTH chipset, Wi-Fi chipset, mobile data network chipset (e.g., 3G chipset, 4G LTE chipset), near field communication (NFC) chipset) and a wired chipset and interfaces 218 (e.g., universal serial bus (USB) interface). The I/O interface 214 can use one or more communication protocols (e.g., internet protocol (IP), BLUETOOTH protocol, Wi-Fi protocol) to communicate with the controller 206 and/or the computer system 202. The encryption chipsets 209 can be used in combination with the I/O interface 214 to encrypt and decrypt information that is communicated to and received from the controller 206 and/or the computer system 202.

For example, the device 206 can communicate with the controller 204 over a network 228, such as a point to point BLUETOOTH network (e.g., BLUETOOTH Low Energy (BLE)), a multi-point BLE network, a Wi-Fi network (e.g., Wi-Fi Direct network), a local area network (LAN), a wide area network (WAN), a virtual private network (VPN), the internet, or any combination thereof. The communication with the controller 204 can be encrypted using one or more appropriate encryption techniques and algorithms. For example, the device 206 can encrypt all packets that are transmitted to the controller 204 using AES in GCM mode with 24 bit cyclic redundancy checking (CRC) and the encrypted packets can be transmitted over a BLE network with 128 bit AES, and can receive encrypted packets from the controller 204 using a similar encryption scheme.

In another example, the device 206 can communicate with the computer system 202 using a communication channel that passes through the controller 204. For instance, the controller 204 can establish a network connection with the device 206 over the network 228 and another network connection with the computer system 202 over another network 258 (e.g., internet, WAN, LAN, mobile data network, Wi-Fi network, or any combination thereof), and can retransmit communication between the device 206 and the computer system 202. Such pass-through communication can be encrypted from endpoint to endpoint by the device 206 (using the encryption chipset 209) and the computer system 202 so as to make the communication private (indecipherable to the controller 204 and any other computing devices along the communication path). For example, all packets transmitted by the device 206 to the computer system 202 can be encrypted with AES in GCM mode, and all packets transmitted by the computer system 202 to the device 206 can be encrypted with AES in GCM mode as well. The communication over the network 228 can using additional layers of encryption, such as BLE with 128 bit AES encryption. The communication over the network 258 can also include additional layers of encryption, such as a secure socket layer (SSL) between the computer system 202 and the controller 204. In some cases, the network 228 and the network 258 can be different communication networks, while in other cases the network 228 and the network 258 can be the same communication network.

The communication pathways over the networks 228 and 258 can be encrypted and authenticated by the sender, and also authenticated and decrypted by the receiver. The computer system 202, the controller 204, and the device 206 can be programmed to implement these encryption and authentication techniques when acting as senders and receivers, which can use message authentication codes and/or signatures to insure the integrity of all data and the identity of the senders on top of data transport supplied integrity checks. Using these security policies, the system 200 can prevent against a random software bug as well as an attacker modifying/observing cleartext traffic or initiating/responding to any commands issued by the computer system 202, the controller 204, and/or the device 206.

The device 206 further includes a device identifier 220 that can be observed and/or obtained by the controller 204 only in certain circumstances, such as when the controller 204 is physically near the device 206 (e.g., visible to the controller 204, within NFC communication ranges, within BLUETOOTH communication ranges). For example, the device identifier 220 can be a code (e.g., barcode, QR code) or other information (e.g., text, symbols, markings) that are imprinted on, affixed to, visible, or otherwise detectable on one or more surfaces (e.g., external housing surface, internal housing surface) of the device 206. In another example, the device identifier 220 can be encoded within one or more chips, beacons, or sensors that are located within or affixed to the device 206, and that are wirelessly detectable by the controller 204, such as a passive or active RFID tag. The device identifier 220 may be implemented on the device 206 and detected by the controller 204 in other ways as well. The device identifier 220 can uniquely identify the device 206 with regard to other devices that are hosted/supported by the computer system 202 (e.g., serial number for the device 206, unique identifier generated by the computer system 202), and/or with regard to a broader universe of devices that are network connectable (e.g., MAC address for the device 206).

The device 206 can be any of a variety of different types of devices and can provide features that may be beneficial to a user, such as delivering medicine to users (e.g., drug delivery system), performing health monitoring and alerting features (e.g., personal fitness/wellness monitors), and/or providing health therapy (e.g., pacemaker devices). The device 206 can include one or more additional components that implement these features, such as a drug delivery system 226 (e.g., insulin pump). An example of the device 206 with a drug delivery system is described below with regard to FIGS. 9A-C.

The device 206 can optionally include one or more portable power sources 224 (e.g., batteries) that are used to provide operational power to the components 208-220 and 226 of the device 206.

As described above with regard to FIG. 1, in some cases the device 206 does not include a robust user interface, such as an output subsystem (e.g., display, speaker) and an input subsystem (e.g., touchscreen, keys/buttons, microphone) that can readily convey and receive information (e.g., text, symbols, words, commands) from a user. In such cases, the device 206 may still include one or more components to convey basic information (e.g., status information, binary or trinary information to the user) through, for example, LED lights. As described above with regard to FIG. 1, the device 206 can be programmed to perform operations to ensure secure communication with the controller 204 and the computer system 202.

The controller 204 can be any of a variety of appropriate computing devices, such as a mobile computing device (e.g., smartphone, tablet computing device, wearable computing device), a desktop computer, a laptop, and/or other appropriate computing devices. The controller 204 includes one or more processors 230 (e.g., CPU, microprocessors, graphics processing units (GPU)), one or more encryption chipsets 232 (e.g., crypto processors), and one or more local storage devices 244 (e.g., flash memory, hard drive, solid state drive) that are programmed to store encrypted data 246 (e.g., private information, patient data, dosing models, application data), an operating system 248 (e.g., iOS, ANDROID operating system, WINDOWS, LINUX), and applications 250 (e.g., mobile applications).

The applications 250 include, for example, a device controller application 252 that is downloadable onto the local storage device 244 (e.g., downloadable from an app store, downloadable from the computer system 202) and is programmed to perform operations to control and optimize operation of the device 206. For example, the controller application 252 can be programmed to transmit control signals to the device 206, to receive operational data from the device 206 (e.g., data describing operations that are performed and user feedback (active and/or passive feedback) in response to the operations), to determine updates to operational models (e.g., dosing models) that are used by the device 206, and to transmit control signals to use the updated operational models.

The device controller application 252 can be signed and authenticated by the computer system 202. Additionally, the device controller application 252 can be programmed to use the processors 230 and the encryption chipsets 232 to encrypt all data that is stored locally by the device controller application 252 and to store it as encrypted data 246, and can be programmed to encrypt all packets that are transmitted to the device 206 and/or the computer system 202. Furthermore, the device controller application 252 can be configured to establish a secure network connection, such as a BLE connection using AES in GCM mode, with the device 206 not having a robust user interface, but instead by using a shared secret (between the device 206 and the controller 204) that is obtained from a trusted third party, such as the computer system 202. The communication between the device controller application 252 and the computer system 202 can be via SSL, over a mutually authenticated, encrypted channel (e.g. the mobile app validates it is talking to the proper web service, and the web service validates it is talking to a specific, authorized, valid mobile app). All packets can further be encrypted by AES-256 in GCM mode and authenticity verified by the receiver.

The applications 250 also include a barcode reader application 254 and/or an RFID reader application 256 that are programmed to detect, for example, the device identifier 220 of the device 260. For example, the barcode reader application 254 is programmed to access a digital camera of the controller 204 to obtain images (and/or videos) of the device identifier 220 and to perform image processing operations to detect, analyze, and identify the device identifier 220 encoded on the device 206. Similarly, the RFID reader application 256 is programmed to detect the device identifier 220 through the use of passive and/or active RFID tags that are associated with the device 206.

The controller 204 additionally includes an input subsystem 234 and an output subsystem 236 through which the controller 204 can provide a user interface to receive input from a user and to provide output to the user, respectively. The input subsystem 234 can include any of a variety of devices through which input from a user can be detected or otherwise obtained from a user, such as a touchscreen (or other touch sensitive surfaces), keys (e.g., keyboard), buttons, motion sensors (e.g., accelerometer, gyroscope), microphones, and/or other appropriate input devices. The output subsystem 236 can include any of a variety of devices through which output can be provided to a user, such as a display, speakers, haptic feedback devices (e.g., devices causing the controller 204 to vibrate), and/or other appropriate output devices. The controller 204 can be different from the device 206 in that the controller 204 can include the more robust input and output subsystems 234-236, through which a user can provide more complex inputs and receive more complex outputs (e.g., text, graphics, instructions).

The controller 204 further includes an I/O interface 238 with a wireless chipset and interface 240 and/or a wired chipset and interface 242. The controller 204 can communicate with the device 206 and the computer system 202 over the network 228 and the network 258, respectively, using the I/O interface 238.

The computer system 202 can include one or more computing devices (e.g., one or more servers) that are programmed to implement a front-end 260 (e.g., web server, application server) and a back-end 262 (e.g., backend processing operations). The front-end 260 and the back-end 262 can be programmed to provide web services for the controller 204 and/or the device 206, and to implement security policies to ensure that all connections and data transmitted across the system 200 are secure. The computer system 202 can include a data storage system 264 (e.g., hard drives, solid state drives, cloud-based storage system) that stores data used by and in association with the computer system 202 as encrypted data 266.

The computer system 202 can implement a variety of usage policies for the system 200. For example, the computer system 202 can restrict the device 206 to being registered with a single user account, but can permit a user account to register multiple devices (like the device 206). The computer system 202 can permit the device 206 to be controllable by the controller 204 (once authorized and verified) when it is web connected to the computer system 202 over the network 258 as well as when it is web disconnected (no connection over the network 258). The computer system 202 can require that the controller 204 be online (connected over the network 258) in order to register/add the device 206 to the user's account, but can permit the controller 204 and the device 206 to be paired with each other while the controller 204 is offline (not connected over the network 258). Such usage policies can be implemented by the computer system 202, the device controller application 252, and/or through commands that are transmitted to that application 252 by the computer system 202.

The computer system 202, the controller 204, and the device 206 can use one or more encryption algorithms to establish secure channels of communication and to encrypt data that is stored locally by each of the devices 202-206. For example, 2048 bit Rivest-Shamir-Adelman (RSA) and/or Elliptical Curve Cryptography (ECC) 224 can be used for asymmetric keys and certificates, and all actors can be first authenticated using mutual authentication via an asymmetric key and then authenticated with a symmetric key using an authentication code (e.g., AES-GCM mode) for ongoing encryption and authentication. In another example, 128 bit AES can be used for all encryption, and AES in GCM mode can be used when encryption and authentication is needed. In a further example, secure hash algorithms, such as SHA-256, can be used for hashes, and in some cases data encryption standard (DES) techniques may not be used. Keys can be exchanged using any of a variety of appropriate techniques, such as Diffie-Hellman (DH) key exchange). True Random Number Generators (TRNG) can be used to seed Pseudo Random Number Generators (PRNG), such as on power on, and can be used for random number and key generation. Key derived functions (KDF) can be based on, for example, SHA-2.

FIGS. 3-8 are flow charts of example techniques 300, 400, 500, 600, 700, 800, and 850 for establishing secure connections and securely communicating among an example computer system 302, an example controller 304, and an example device 306. The example computer system 302 can be any of a variety of appropriate computer system, such as the computer systems 102 and/or the computer system 202. The example controller 304 can be any of a variety of appropriate computing device, such as the controller 104 and/or the controller 204. The example device 306 can be any of a variety of appropriate device, such as the device 106 and/or the device 206. The example techniques 300-850 can be performed separately and/or together in any of a variety combinations or permutations.

Figure 3:
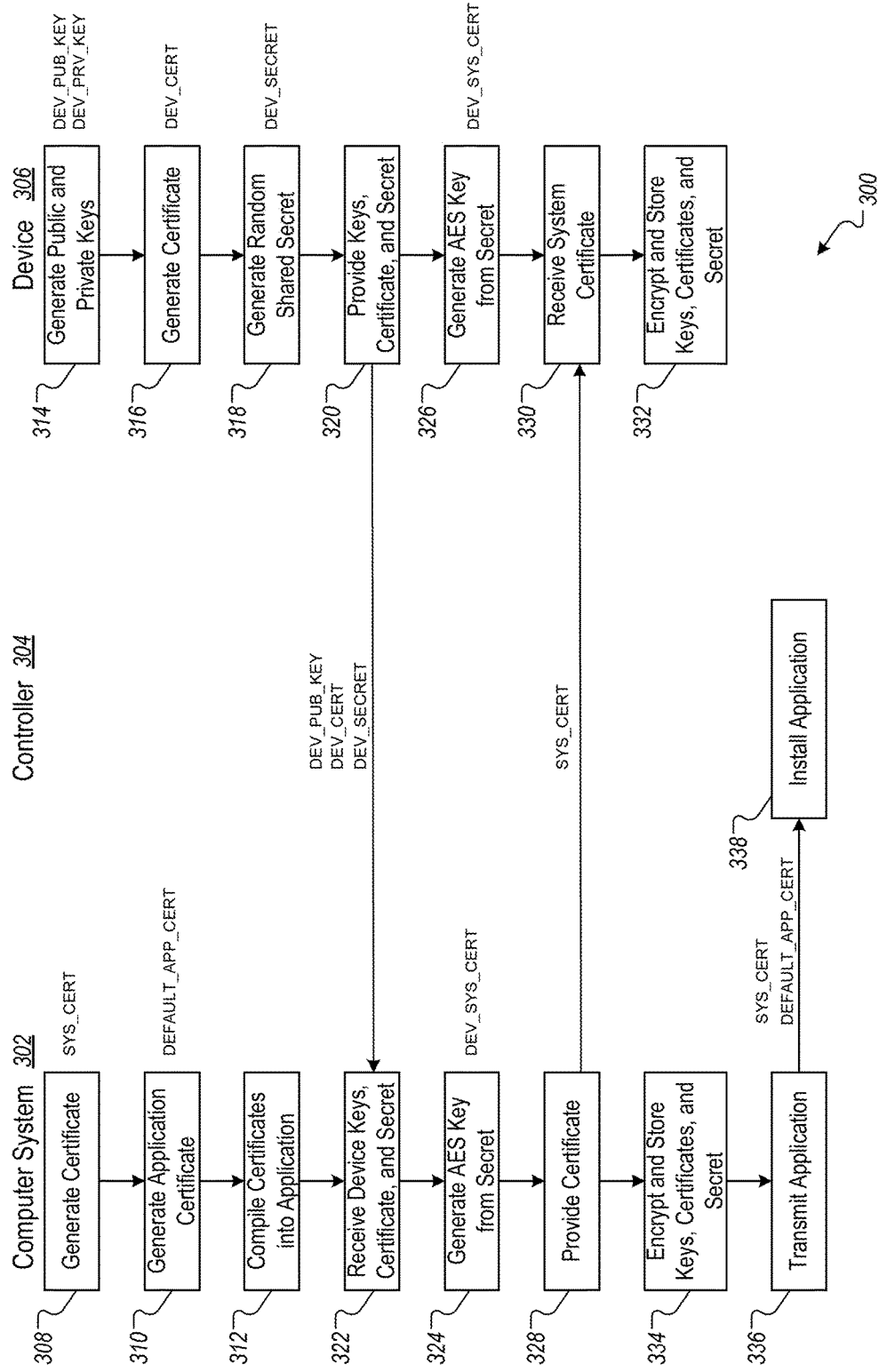
FIG. 3 is a flowchart of an example technique for establishing keys and certificates with the computer system.

Referring to FIG. 3, which depicts the example technique 300 for establishing keys and certificates with the computer system 302. The example technique 300 can be performed before the device 306 is shipped/sold/distributed, and can include the computer system 302 generating a public authentication certificate (e.g., SYS_CERT) that can be distributed to the controller 304 and the device 306 to verify/sign transmissions from the computer system 302 (308). The computer system 302 can also generate a default application certificate (e.g., DEFAULT_APP_CERT) that can be distributed with an application to be installed on the controller 304 to verify/sign transmissions from the controller 304 (310). The computer system 302 can compile the system and default application certificates into an application binary that is to be distributed to the controller 304 (312).

The device 306 can generate a keypair of public and private keys (e.g., DEV_PUB_KEY, DEV_PRV_KEY) that are provisioned on the device 306 (314). For example, the device 306 can use a crypto chip filesystem that is written and initialized to generate and locally store the key pair. The device 306 can also generate an authentication certificate (e.g., DEV_CERT) that can be used to sign/verify transmissions from the device 306 (316). The certificate and the key pair can be stored with encryption on the device 306 using, for example, a crypto processor that is part of the device 306. The device 306 can also generate a random shared secret (e.g., DEV_SECRET) that will be provided to the computer system 302 to create a symmetric key (e.g., AES-GCM key) across the system 302 and the device 306. The device 306 can provide the public key, the certificate, and the shared secret to the computer system 302 (320), which can receive that information (322).

The computer system 302 and the device 306 can use the shared secret to generate a shared key, such as an AES key (324, 326). For example, both the computer system 302 and the device 306 can use an agreed upon encryption function, such as an Encryption Key Derivation Function (KDF), to generate a shared symmetric key, such as an AES-GCM key. The computer system 302 can additionally provide the system certificate (e.g., SYS_CERT) to the device 306 (328), which can receive the certificate (330) and can encrypt and store it with the other keys and certificates generated by the device 306 (332). For example, the device 306 can use a crypto processor to store the certificates and keys as encrypted values in a local files system on the device 306. The system 302 can also encrypt and store the keys, certificates, and secrets (334)

The computer system 302 can transmit the application compiled with the certificates to the controller 304 (336). For example, the controller 304 can request the application from the computer system 302 and/or other computer system (e.g., app store). The controller 304 can receive and install the application (338), which can include the system certificate and the default app certificate.

Figure 4A:
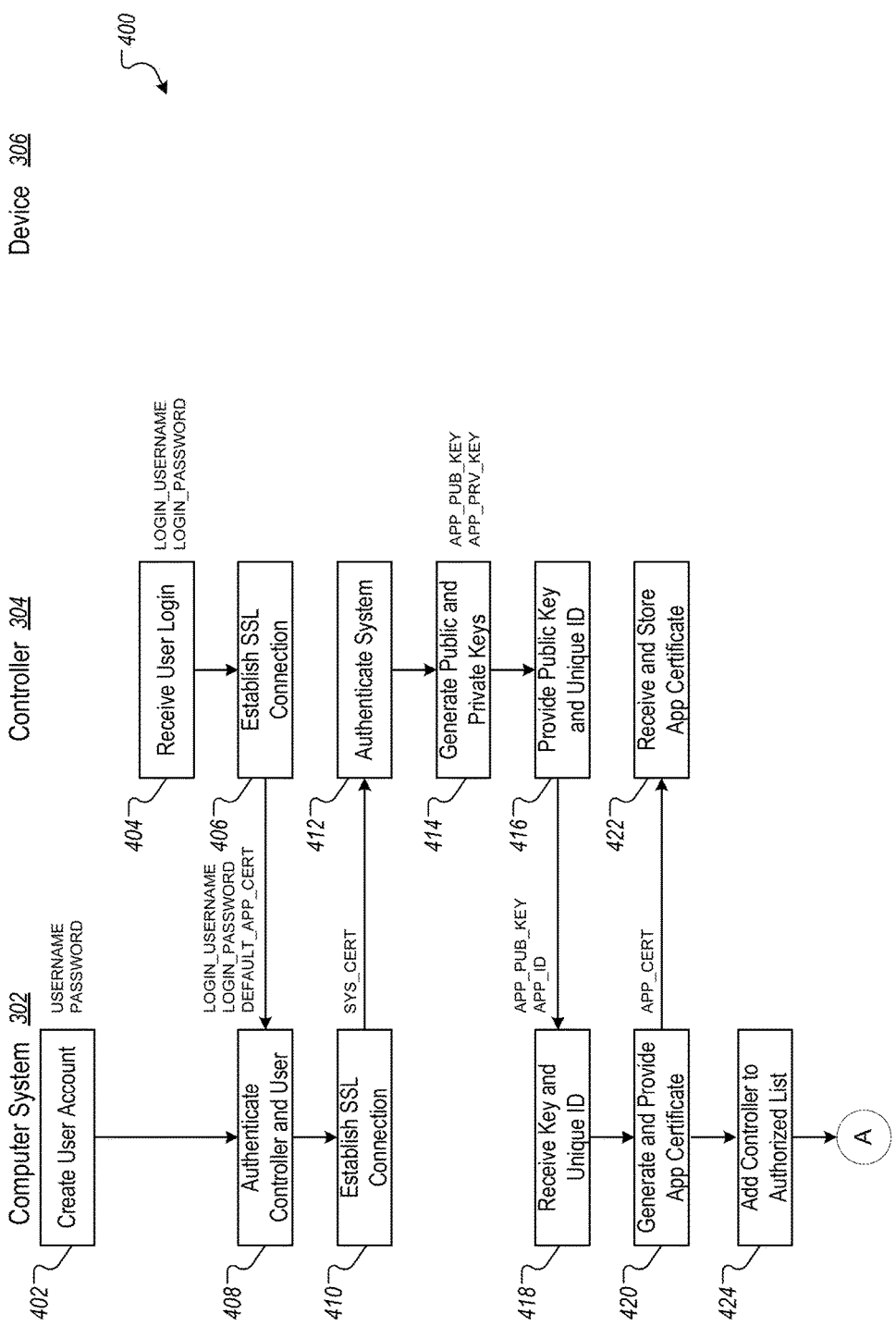
FIGS. 4A-B are flowcharts depicting an example technique for creating a user account and registering an application on the controller with the computer system.
Figure 4B:
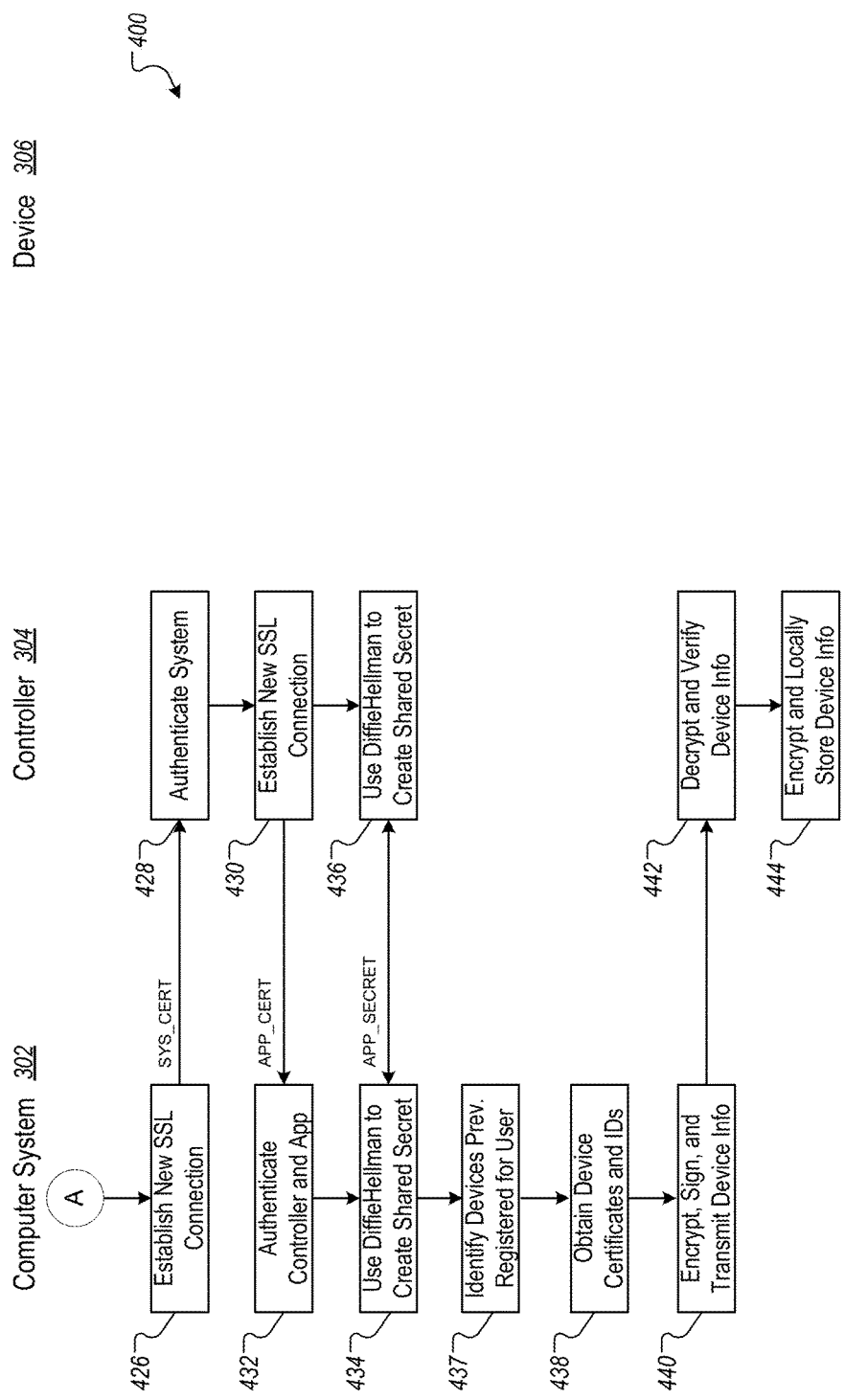

FIGS. 4A-B are flow charts depicting an example technique 400 for creating a user account and registering an application on the controller 304 with the computer system 302. The example technique 400 may be performed after one or more portions of the example technique 300 are performed.

The technique 400 can include creating a user account (402). For example, a user can log into a cloud service hosted by the computer system 302 and initialize a user account. This can be done, for example, from a web page and/or from a mobile app. To create a user account, the user may be required to: choose username (the computer system 302 can validate uniqueness), choose a password (the computer system 302 can validate password strength), add email address/phone number/contact info (the computer system 302 may validate), and verify registration with a confirmation email.

With a user account created, a user can log into his/her account from the application installed on the controller 304, which can receive the user login information (404). The login can unlock the default application certificate (e.g., generic app certificate compiled into the app binary and signed) and key stored on the controller 304. The controller 304 can use the certificate and login information to create an initial mutually authenticated SSL connection between the controller 304 and the system 302 (406-408). The app and user are is authenticated by computer system 302 with password and certificate (clientauth). The computer system 302 can then be authenticated by the application using the computer system public certificate (e.g., SYS_CERT) which is also compiled into the binary (e.g. certificate pinning) (410-412).

If there is no existing user-specific certificate on the controller 304, this mutually authenticated channel with the computer system 302 can be used to generate a new certificate. As part of the new certificate, the application on the controller 304 can generate an asymmetric key pair (e.g., APP_PUB_KEY, APP_PRV_KEY), and passes the public key with a unique identifier (e.g., controller identifier (e.g., phone uniqueID (IDFV), application identifier) with a certificate request to the computer system 302 (416), which can receive the key and the unique identifier (418).

The computer system 302 can generate a user-specific certificate (e.g., APP_CERT) and provide it back to the controller 304 (420), which can receive and store the app certificate (422). The computer system 302 can add the controller 304 to an authorized list (e.g., add smartphone UniqueID, add app identifier) and can add public key to a database in association with the controller 304 (424).

Referring to FIG. 4B, the computer system 302 and the controller 304 can establish a new mutually authenticated SSL channel to generate a shared secret that will be used for sending messages with symmetric key encryption (e.g., AES in GCM mode) between the computer system 302 and the controller 304 (426-432). Using the new SSL channel, the controller 304 and the computer system 302 can use Diffie-Hellman encryption to establish a shared secret (e.g., APP_SECRET) between them (434, 436). Now the computer system 302 and the controller 304 have each other's public key as well as a shared secret that can be used to generate a symmetric key between them (e.g., AES-GCM key).

The mutually authenticated SSL channel can be used to provide the controller 304 with information to authenticate devices that are already registered with the user's account that is now associated with the controller 304. If there are no previously registered devices, steps 438-446 may not be performed. If there are previously registered devices, the computer system 302 can identify previous devices that are registered for the user (437), obtain certificates and identifiers for those devices (438), and transmit them to the controller 304 (440). For example, the computer system 304 can download blob (if there are any) with public DEV_CERT(s) that have previously registered device serial numbers that this user is authorized to be connected to and authorized identifier for the controller (e.g., phone UUID's). The blob can be encrypted with the public key or the symmetric key between the system 302 and the controller 304, and can be signed with certificate for the computer system 302.

The controller 304 can then decrypt and verify the device information (e.g., blob) using the private key and/or the symmetric key between the system 302 and the controller 304 (442). For example, the controller 304 can verify the blob with the certificate for the computer system 302 that was compiled into the app.

The example technique 400 (and other techniques 300 and 500-850) can provide any of a variety of protections and advantages. For example, these techniques can, individually or in one or more combinations, ensure that the computer system 302 is communicating with an authentic app on the controller 304, that the app on the controller 304 is communicating with an authentic service on the computer system 302, that the controller 304 is only communicating with devices that are registered to the user, that the device 306 can only communicate with an authorized user on an authorized app, that communications between the computer system 302, the controller 304, and the device 306 are encrypted and mutually authenticated, and/or that a device policy allows the device 306 to be a data driven mechanism to enforce which commands it will respond to and which ones it will not. Any commands that are not expressly allowed in policy will be can be ignored by the device 306.

FIGS. 5A-D are flow charts that depict an example technique 500 for pairing the controller 304 to the device 306, and for adding the device 306 to a user account. The example technique 500 can be performed, for example, in combination with (and after) the techniques 300 and 400 described above.

A user can login enter login information on the controller 304 (502) that can be used to authenticate the user and controller, and to establish a mutually authenticated SSL connection between the controller 304 and the computer system 302 (503-506). Once logged in on the controller 304, the user can (e.g., from a button or a menu) obtain a device identifier (e.g., serial number), such as by the user entering the device identifier into a user interface or by optically scanning (e.g., red laser scanning) the device identifier (508). Using the SSL connection, the controller 304 can request information for the device 306 by transmitting the device identifier to the computer system 302 (510), which can receive the request and determine whether the device has already been allocated to another account (512). The computer system 302 may have a policy that each device can only be registered with one user account, but may be registered with multiple controllers that are associated with the same user account. If the device 306 is already registered with another account, the computer system 302 can deny the request, which can prevent against malicious registration/misappropriation of the device 306. If the device 306 is not registered with an account, the computer system 302 can retrieve and transmit device information, such as a public key for the device 306 and the public certificate for the device 306 that were created and provided to the computer system 302 as part of the technique 300 (514). The controller 304 can receive and store the device information (516).

With the device information, the controller 304 and/or the device 306 can initiate a pairing process (e.g., the user can select the device 306 from a list of authorized or nearby devices on the app), such as a secure BLE pairing process that requires a shared secret between the devices being paired. In this example, the device 306 may not have a user interface, so the shared secret can be one or more portions of the device information, such as a public key for the device, a public certificate, a device identifier, and/or a value determined based on one of those portions of information. For instance, the controller 304 can transmit a challenge that includes a value (e.g., random value) and, using a technique known to the controller 304 and the device 306, can determine an appropriate response (e.g., RESPONSE_A) based on the value and the shared secret (e.g., public key for the device 306) (518). The device 306 can receive the challenge (520), and can determine and transmit the appropriate response based on, for example, the device's public key and the value (e.g., VALUE_A) (522). In some cases, the device 306 can also sign the response using, for example, the public device certificate, which is also known to the controller 304. The controller 304 can receive the response and determine whether it matches the response that the controller 304 independently determined (524). If the values match, the controller 304 can verify that it is communicating with the proper device 306 (526).

Figure 5A:
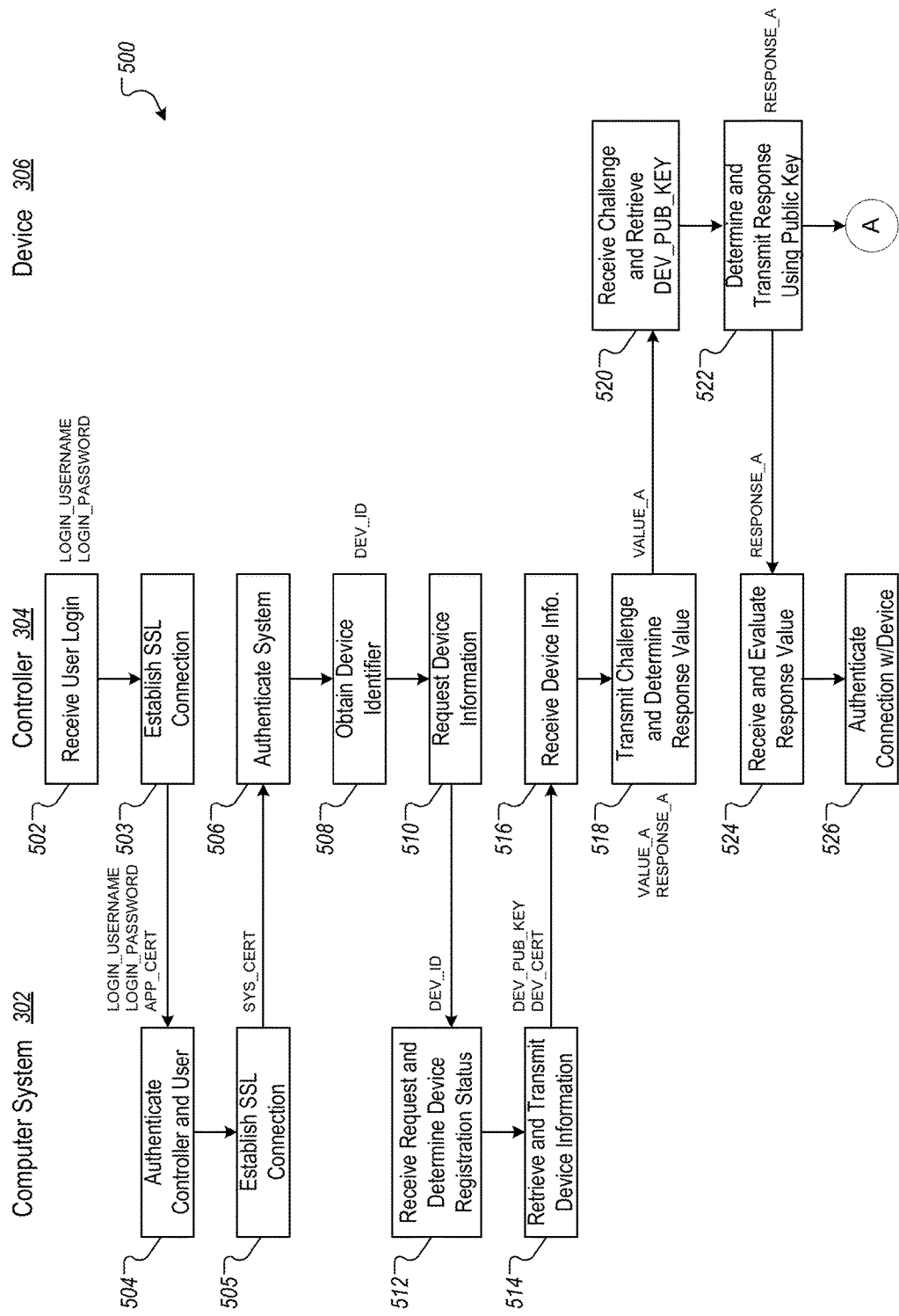
FIGS. 5A-D are flowcharts that depict an example technique for pairing the controller to the device, and for adding the device to a user account.
Figure 5B:
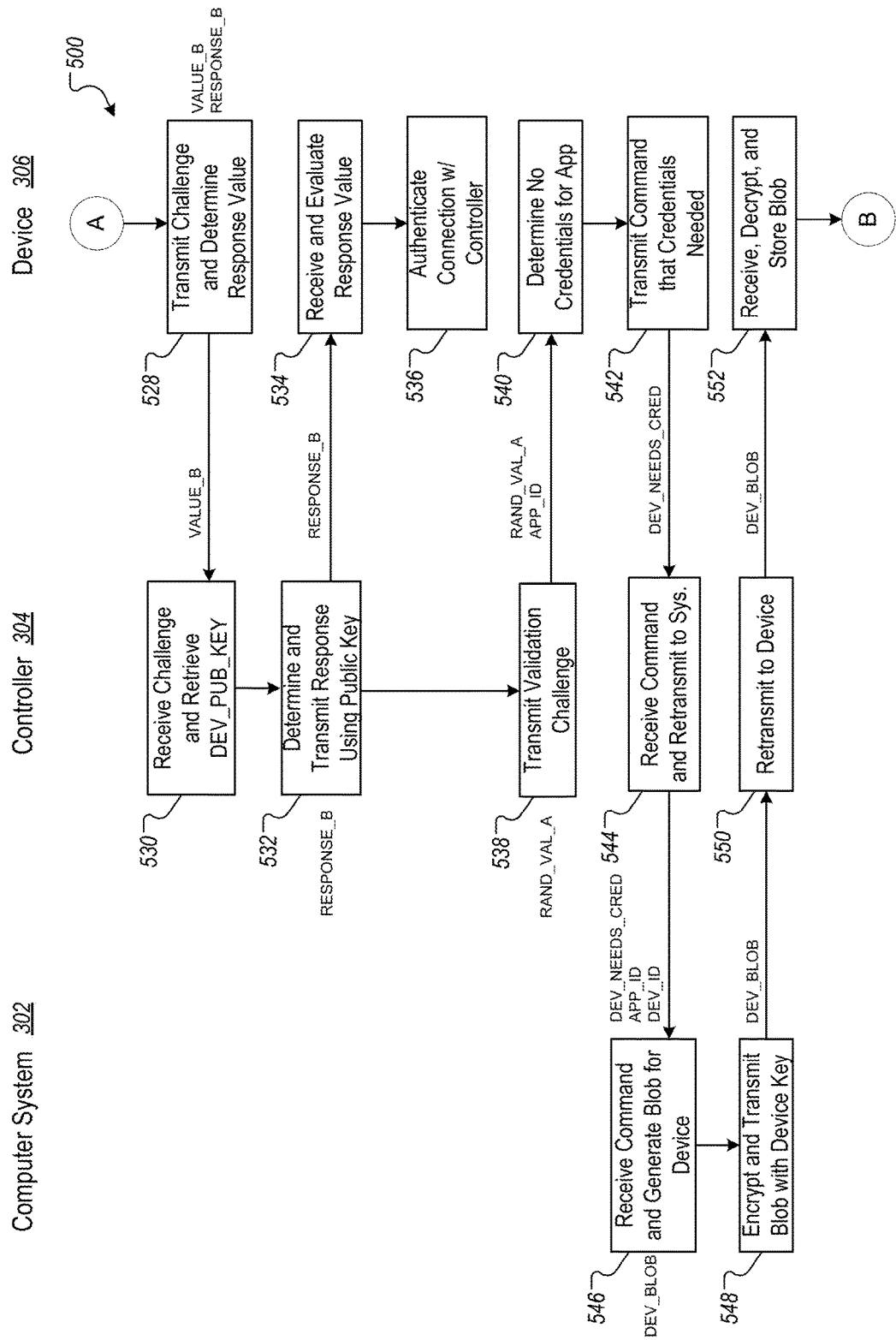

Referring now to FIG. 5B, device 306 can then challenge the controller 304 using a different value (e.g., VALUE_B), resulting in a different response value (e.g., RESPONSE_B) that that is determined from the value and the shared value (e.g., device 306 public key) (528). The controller 304 can receive the challenge (530), and determine and transmit the response (532), which the device 304 can evaluate (534). The response may be signed with, for example, the controller's certificate. The device 306 can determine that the controller 304 is authentic based on the response matching an independently determined response value (536).

After the pairing is complete, the controller 304 can seek to validate the device 306 as being a valid device with the computer system 302. The controller can send the device 304 a validation challenge (538), which can include a random number, along with the a unique identifier for the controller 304 and/or the app. The device 306 can determine whether it has credentials for the app (540), and if no credentials for the app are present, the device 306 can transmit a command to obtain credentials (542). The controller 504 can receive the command indicating that credentials are needed and can retransmit the request to the computer system 302 (544), along with an identifier for the controller 304 (and/or its application) and an identifier for the device. For example, the device 306 can send a message with the device's serial number and the controller's UUID (over the mutually authenticated SSL with the computer system 302). This message can be encrypted using a public key for the computer system 302 and/or a symmetric key established between the computer system 302 and the controller 304. The computer system 302 can receive the command and authenticate that the app/controller 304 and the device 306 are supposed to be in communication with each other, and can generate a blob for the device 306. For example, the device blob can include a certificate for the app on the controller 304, an identifier for the controller 304 (e.g., UUID (IDFV)) and/or its app, and/or an identifier for the device 306 (e.g., serial number). The blob can be encrypted, for example, using a public key for the device 306 and/or a symmetric key between the computer system 302 and the device 306, and can be signed by a certificate for the computer system 302 (548).

The encrypted blob can be sent via SSL to the controller and then retransmitted by the controller 304 over, for example, BLE AES to the device 306 (550). The retransmission can be pass-through—meaning that the controller 304 cannot read or decrypt this message. The device 306 can receive, decrypt, store, and verify the blob (e.g., verify with the certificate for the computer system 302 and the serial number for the device 306) (552). Once verified, the device 306 can imports the app's unique identifier (e.g., generated UniqueID (IDFV)) into its list of approved apps as well as a policy for the device 306 and the controller 304.

Figure 5C:
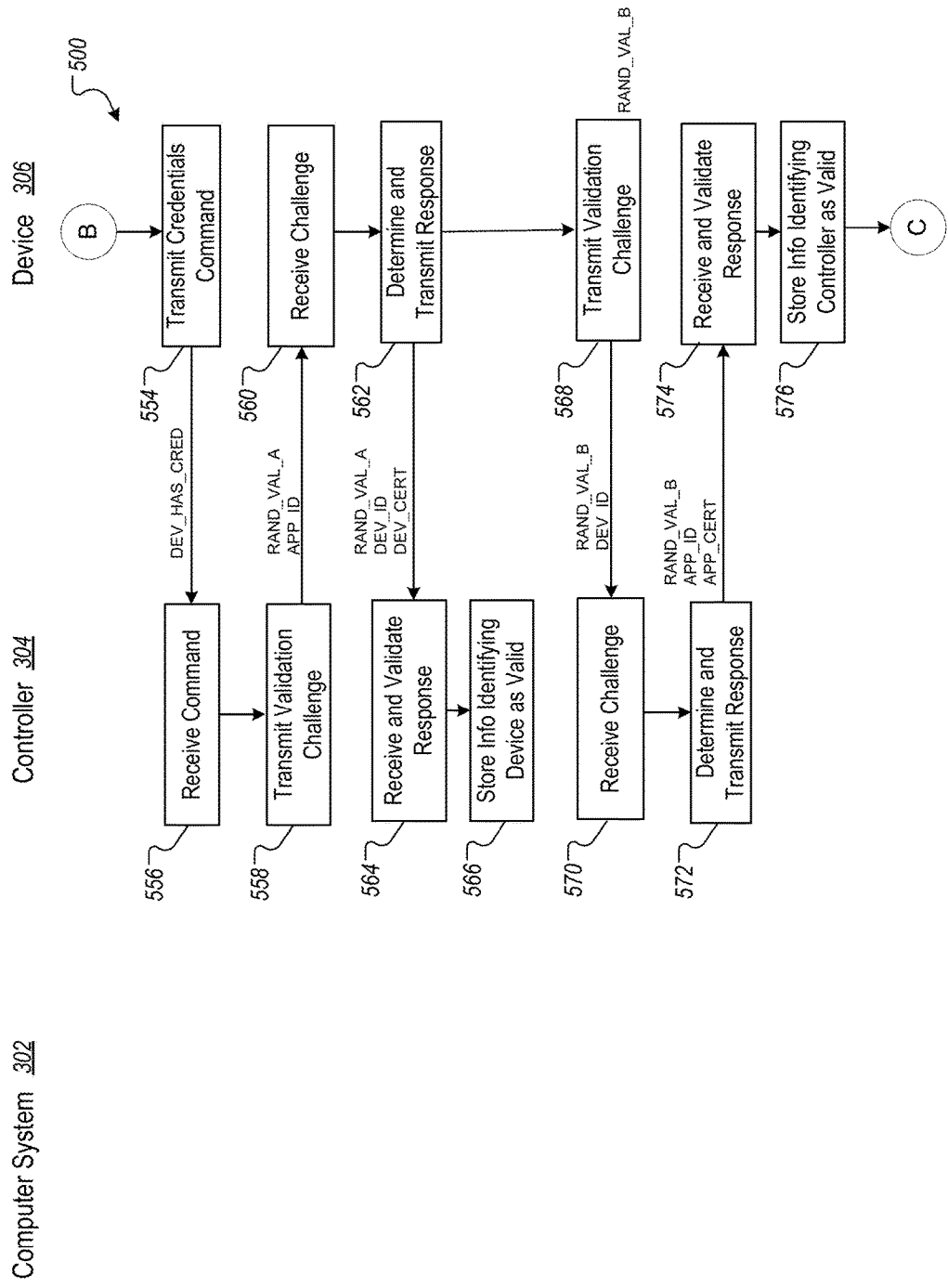

Referring to FIG. 5C, once the device 306 has obtained credentials for the controller 304 from the computer system 302 in a way that the controller 304 cannot eavesdrop on, the device 306 can transmit a command indicating that it now has credentials (554), which can be received (556) and can cause the controller 304 to retransmit the validation challenge (558). The device 306 can receive the challenge (560), and can determine and transmit a response (562). The response can include, for example, a unique identifier for the device 306 (e.g., serial number) and the random value, and can be signed with the certificate for the device 306. The controller 304 can receive and validate the response (564), for example, by verifying that the random number and the unique identifier for the device 306 are correct, and that the response is validly delivered by the device 306 (signed by the certificate for the device 306). In response to determining that the device 306 is valid, the controller 304 can store information locally identifying the device 306 as valid (566).

The device 306 can perform a similar validation process for the controller 304. For example, the device 306 can generate a random value (e.g., 32 bit challenge) and can send it as a challenge to the controller 304 along with a unique identifier for the device 306 (568). The controller 304 can receive the challenge (570) and can determine and transmit a response (572) that includes a unique identifier for the controller 304 and/or its application and the random value, which can be signed by the application's certificate. The device 306 can verify the message using the controller information and certificate that it obtained for the application (APP_CERT) from the computer system 302 (574), and can add the controller 304 to a list of known good devices (576).

Figure 5D:
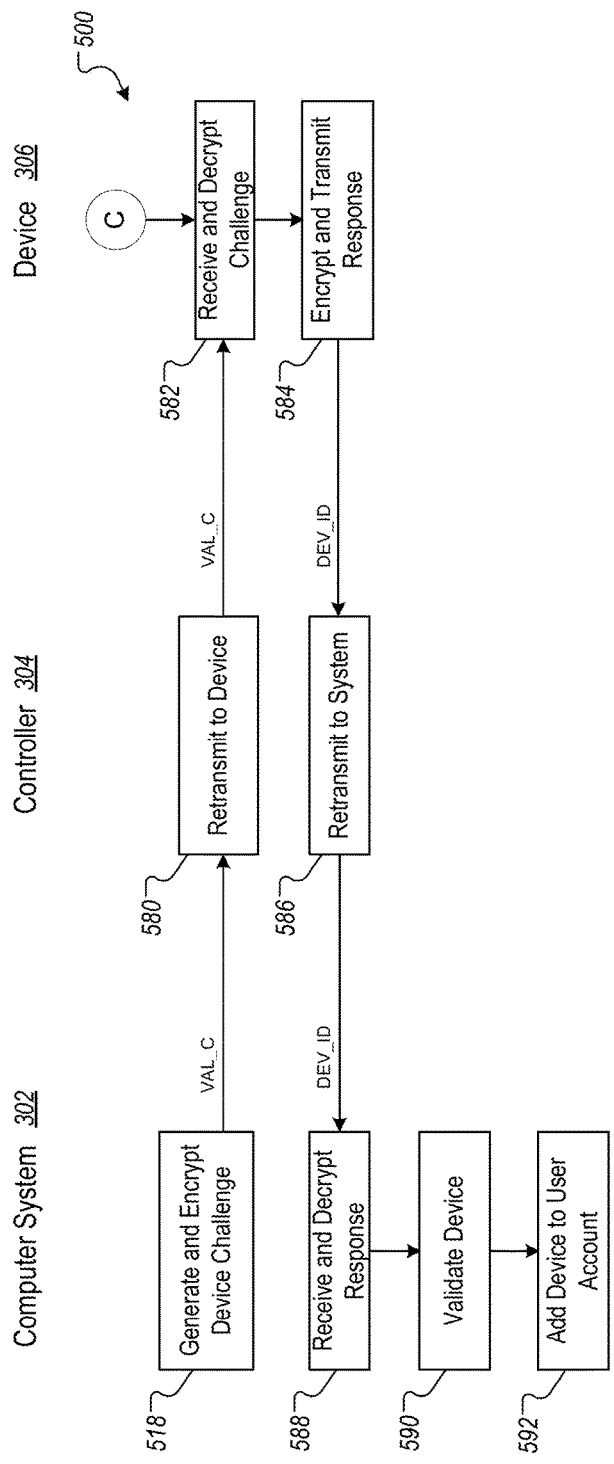

Referring to FIG. 5D, once the controller 304 and the device 306 have cross-validated each other, the computer system 302 can send down a device challenge to the device 306 encrypted with an appropriate encryption key (e.g., public key for the device 306, symmetric key between the computer system 302 and the device 306) (578). The challenge can be retransmitted through the controller 304 (580), but may not be viewable by controller 304 based on its encryption. The device 306 can receive and decrypt the challenge (582), and can determine and encrypt a response that is sent back to the computer system 302 (584). For example, the device response can be a unique identifier for the device 306 (e.g., serial number) that is encrypted with an appropriate key (e.g., public key for the device 306, symmetric key between the computer system 302 and the device 306). The response can be retransmitted by the controller 304 (586) and received by the computer system 302 (588). The computer system 302 can decrypt the message and validate the device 306 (590) based on the decrypted values (e.g., decrypted value matches serial number for device 306). The computer system 302 can add the device to an account associated with the user (592).

The example technique 500 can provide any of a number of advantages and security protections. For example, the technique can allow devices to only be added to accounts authorized by the computer system 302, recycling the device 306 to another user can be done securely, the computer system 302 can retain control of which users can add which devices to their profile/account, apps can only be paired with valid devices, the device 306 can only be paired with a valid app and with a valid and authorized user, and BLUETOOTH pairing can be securely accomplished without the device 306 including a UI or needing user intervention.

Figure 6:
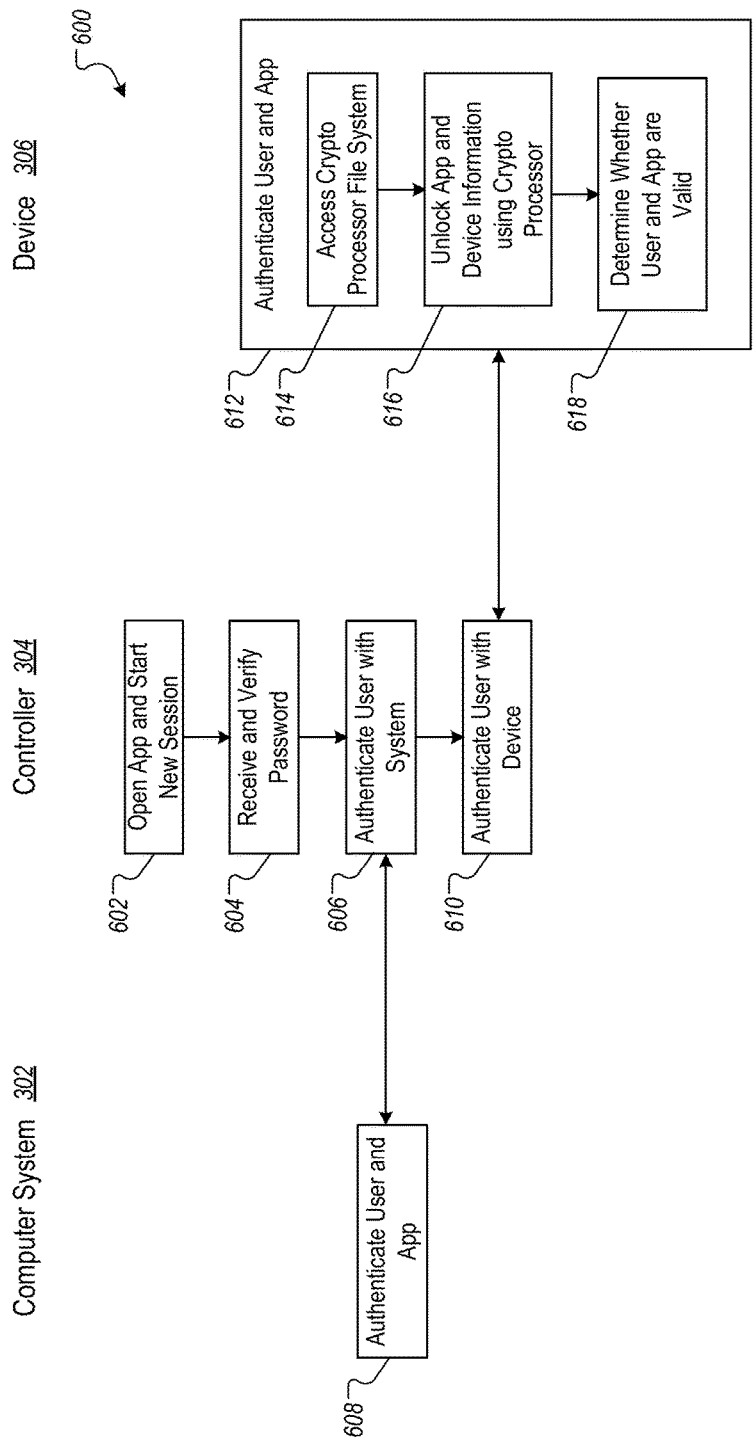
FIG. 6 is a flowchart that depicts an example technique for starting a new session on an application running on the controller.

FIG. 6 is a flowchart that depicts an example technique 600 for starting a new session on an application running on the controller 304. The example technique 600 can be performed, for example, in combination with (and after) the techniques 300-500 described above.

A user can open an app and start a new session on the controller 304 (602), and can receive and verify a password from the user (604). A password may not need to be entered at the start of every session, there may be an option to enable authentication persistence so that user does not have to enter password every time. Passwords can also be through alternative verification techniques, such as through a biometric scanner and API, when available. The controller 304 can authenticate the user with the system 302 (606, 608), which can be over a mutually authenticated SSL connection, which may not require a password. The controller 304 can additionally authenticate the user with the device 302 (610, 612), such as over a BLUETOOTH AES channel. The device 302 can authenticate on a crypto processor with certificate, such as authenticating against a crypto processor file system node (dependent on crypto processor). For example, the device 306 can access a crypto processor file system (614), which can unlock device and application information (616), such as a device policy, an app certificate, computer system authentication keys, application authentication keys, a computer system certificate, and/or a device certificate. Such values may have been encrypted by the crypto processor on the device 306 with a random AES key and the user's password, and may have been stored in an operating system keychain. Such decrypted values can be used to determine whether the user and the app on the controller 304 are authentic/valid (618).

The example technique 600 can provide any of a number of advantages and security protections. For example, the controller app can be connected to an authenticated computer system 302 and device 306. The operating system (e.g., iOS) keychain can protect certificates and keys from modification and tampering, and the operating system signing mechanism can be used to protect applications from modifications.

Figure 7:
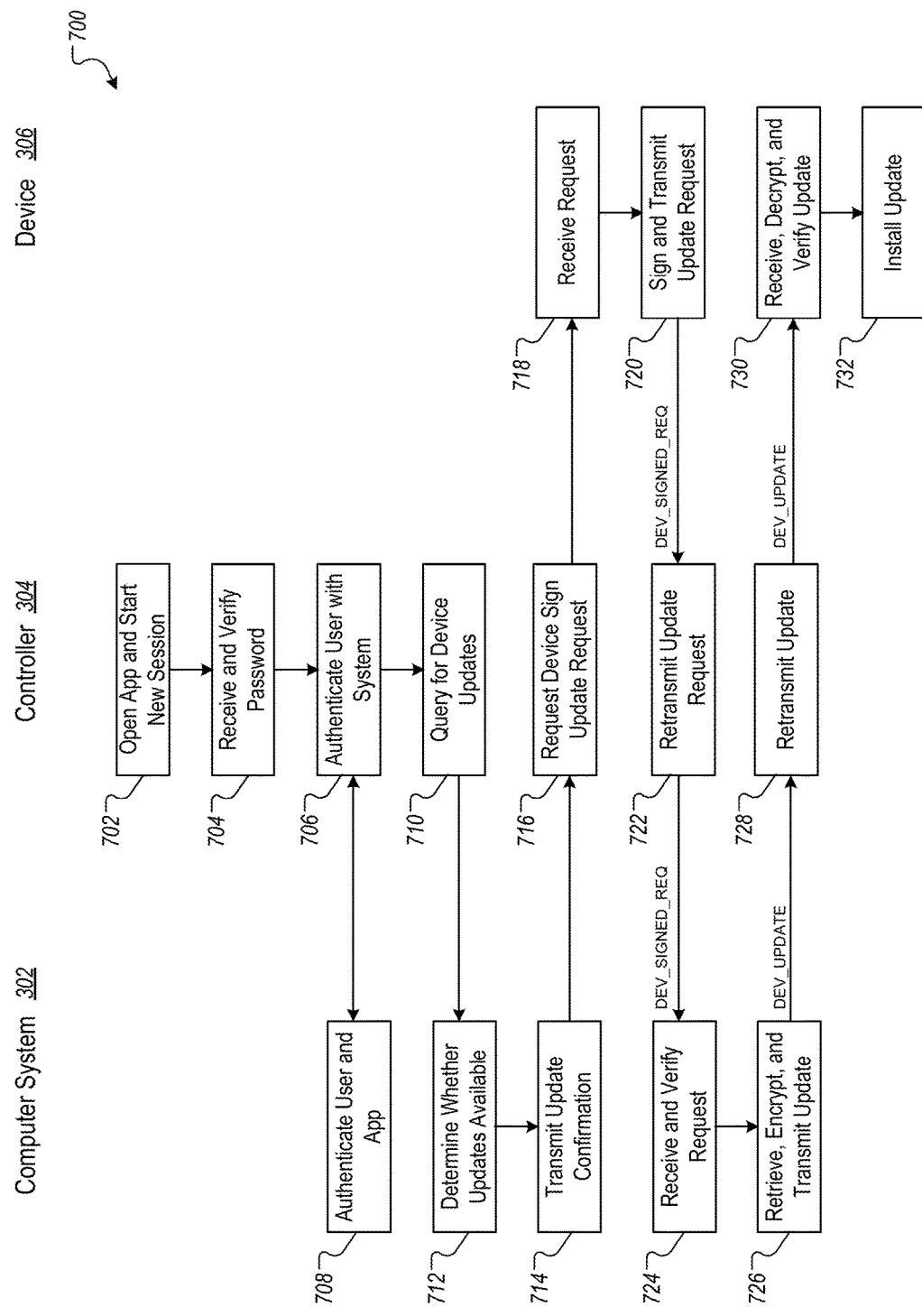
FIG. 7 is a flowchart of an example technique for applying updates to the device.

FIG. 7 is a flowchart of an example technique 700 for applying updates to the device 306. The example technique 700 can be performed, for example, in combination with (and after) the techniques 300-600 described above.

The steps 702-708 involve a user logging in and being authenticated by the controller 304 and the computer system 302 over a mutually authenticated SSL connection, similar to the technique 600. Once authenticated, the controller 304 checks with the computer system 302 to see if there are any updates available for the device 306 (708). The computer system 302 determines whether any updates are available and returns confirmation that updates are available (712-714). In response to receiving confirmation that updates are available, the controller 304 can request that the device 306 sign an update request along with, for example, its unique identifier (e.g., serial number) and current operating system/firmware version (which can prevent firmware service DDOS attack) (716). The device 306 can receive the request (718) and can sign the update request (720), which can include be with the device's authentication certificate and/or encrypted with an appropriate key (e.g., public key for the computer system 302, symmetric key for the computer system 302 and the device 306), which can be authenticated by the computer system 302.

The controller 304 can receive and retransmit the signed update request (722), which can be received and verified by the computer system 302 (724). In response to verifying the request, the computer system 302 can retrieve, encrypt and transmit the update to the device 306 (726). For example, the computer system 302 can send firmware updates that are AES-GCM encrypted and GMAC'd with a new version field in the header. Such a firmware update command can include the serial number for the device 306 as one of its parameters. The controller 304 can pass the signed, encrypted update (e.g., firmware update) down to the device 306 (728), which can receive, decrypt and verify the update (730). Such verification can include, for example, checking that the serial number included with the update matches the serial number for the device 306, verifying the downloaded firmware package, and checking that the firmware version is greater than its existing version number.

Once verified, the device 306 can install the update (732). For example, this can include installing the updated firmware into an appropriate slot. For instance, there can be multiple firmware slots (e.g., Firmware Backup, Firmware Current). At various time, such as on bootup, firmware_current can be backed up to firmware_backup (if it has not done so before). New/updated firmware can be installed to the Firmware current slot. Other configurations are also possible, such as a factory reset option and a third firmware slot.

The example technique 600 can provide any of a number of advantages and security protections. For example, firmware can be uniquely encrypted/signed per device (e.g., with the device's serial number) on the computer system 302 and sent via an encrypted channel to the device 306, intermediary devices along the update transmission path, such as the controller 304, never see unencrypted updates/firmware, firmware is restricted to being up-revved, and/or there is a backup firmware copy in case bad firmware is sent to the device.

Figure 8A:
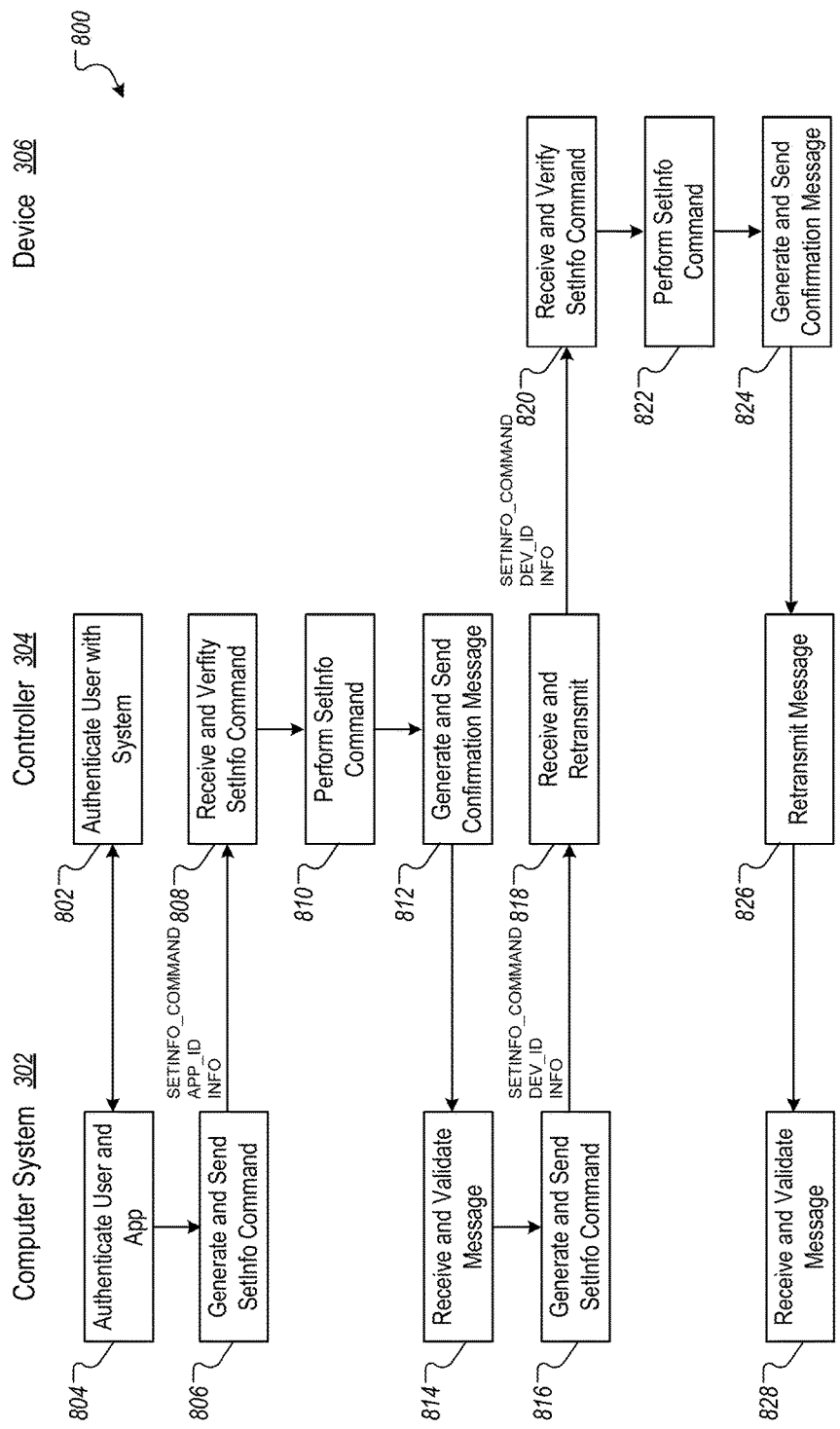
FIG. 8A is a flowchart of an example technique for transmitting settings between the computer system, the controller, and the device.

FIG. 8A is a flowchart of an example technique 800 for transmitting settings between the computer system 302, the controller 304, and the device 306. The example technique 800 can be performed, for example, in combination with (and after) the techniques 300-700 described above.

The controller 304 authenticates a user with the system 302 (802, 804), which can be over a mutually authenticated SSL connection with the computer system 302. The computer system 302 can send a SetInfo command to the controller 304 (806). Such a SetInfo command can include, for example, a unique identifier for the controller 304 (e.g., application identifier, controller identifier) and information that is to be set on the controller 304. For example, the command can include a set_info sequence_id type, selector, buffer, length to controller 304, encrypted and authenticated with AES-GCM using one or more appropriate keys (e.g., AES key, controller 304 public key) over the encrypted SSL channel.

The controller 304 can receive and verify the SetInfo command (808), perform the SetInfo command (810), and can generate and send a confirmation message back to the computer system 302 over the SSL connection (812). Such a SetInfo command can include, for example, application settings, device 306 settings, configuration parameters, and/or other informations/settings. Verification of the SetInfo command can include, for example, verifying the message (e.g., whether signed by an appropriate certificate for the computer system 302) and verifying that a unique identifier matches the identifier for the controller 304 and/or its application. The return message can include the controller 304 encrypting and/or signing the message, such as encrypting the message with an appropriate key (e.g., public key for the computer system 302, AES key between the computer system 302 and the controller 304). The computer system 302 can receive and validate the confirmation message (814).

The computer system 302 can perform a similar set of operations when transmitting SetInfo commands to the device 306 (816-828), but the SetInfo commands and responses with the device 306 can involve retransmission by the controller 304. However, the controller 304 may have no visibility into the message, so there may not be a need for a header/flag in the message, or special API features to differentiate between messages for the device 306 and messages for the controller 304. If the message is for the device 306, the controller 304 can forward the request to the device 306, such as over a secure BLE connection.

The example technique 800 can provide any of a number of advantages and security protections. For example, commands are limited to being processed by the device they are intended for, commands cannot be modified in transit, the controller 304 will be a pass through conduit for device 306 commands and cannot decrypt commands intended for the device 306, communication errors can be caught before processing, commands cannot be replayed, commands are over an encrypted channel that cannot be decoded by an attacker, commands cannot be sent from a rogue service, commands cannot be executed out of order, and/or buffer lengths can be defined and not overrun.

Figure 8B:
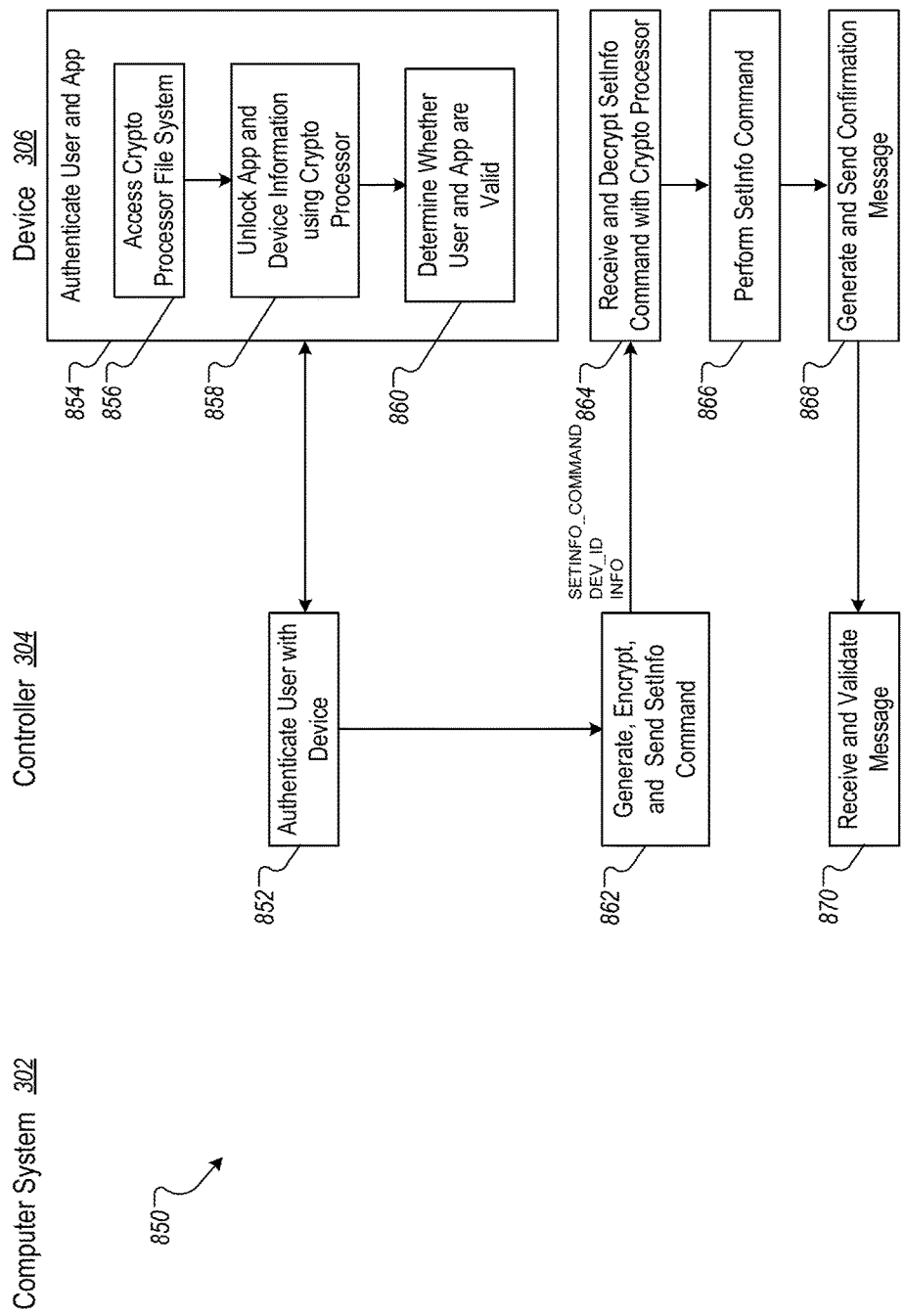
FIG. 8B is a flowchart of an example technique for transmitting settings between the controller and the device.

FIG. 8B is a flow chart of an example technique 850 for transmitting settings between the controller 304 and the device 306. The example technique 850 can be performed, for example, in combination with (and after) the techniques 300-800 described above.

The controller 304 can authenticate the user and with the device 302 (852, 854), such as over a BLUETOOTH AES channel. The device 302 can authenticate on a crypto processor with certificate, such as authenticating against a crypto processor file system node (dependent on crypto processor). For example, the device 306 can access a crypto processor file system (856), which can unlock device and application information (858), such as a device policy, an app certificate, computer system authentication keys, application authentication keys, a computer system certificate, and/or a device certificate. Such values may have been encrypted by the crypto processor on the device 306 with a random AES key and the user's password, and may have been stored in an operating system keychain. Such decrypted values can be used to determine whether the user and the app on the controller 304 are authentic/valid (860).

The controller 304 can generate, encrypt, and send a SetInfo command to the device 306 (862). For example, requests can be encrypted using an AES-CBC key and signing using ECC keys for the controller 304 and device 306, and can be sent over a secure BLE channel. AES in GCM modes can provide both encryption and authentication. The device 306 can decrypt the request on the crypto processor (which can also authenticate the request), check the device's identifier (e.g., serial number) (864) and, if there is a match, can perform the request (866). After performing the request, the device 306 can send back a response (including device identifier) encrypted/GMAC'd using an appropriate key on the crypto processor over the BLE channel (868). The controller 304 can receive and validate the response (870).

The example technique 850 can provide any of a number of advantages and security protections. For example, commands can only be processed by the device they are intended for, commands cannot be modified in transit, communication errors can be caught before processing, commands cannot be replayed (AES-GCM has a counter), commands are over an encrypted channel (and then over encrypted Bluetooth) and thus cannot be decoded by an attacker, and/or commands cannot be sent from a rogue app or controller 304.

The systems, devices, and techniques described above with regard to FIGS. 1-8 (and described below with regard to FIGS. 9-10) can be used to provide any of a variety of secure features between medical devices and other computing devices. For example, secure proximity pairing can be provided between medical devices and computing device (e.g., smartphones) via web services provided through a remote server system. For example, web services can create signed and verified policies that authorize medical devices to communicate with specific controller devices (e.g., smartphones), signed and verified policies that authorize controller devices to communicate with specific medical devices.

In another example, mutual authentication between medical devices, controller devices, and web services can be provided, and can permit for secure communication channels to be established between medical devices, controller devices, and web services. For instance, secure communication channels can include encrypted and/or authenticated communication channels, non-replayable communication (via nonce), and/or encrypted communications (control and data) between web services and medical devices that pass through controllers devices which cannot read or modify the communication.

In a further example, root of trust on medical devices can authenticate all communication to the medical devices and can ensure that only authorized (enabled and allowed) commands from controller devices will be executed by the medical devices. Parametric algorithms on medical devices, controller devices, and web services can be used to ensure normalization of parameters across the devices/services. User authentication may be required for commands specified on a device policy which is authenticated by root of trust on the medical devices. Secure medical device firmware can be authenticated by key on root of trust. Controller devices can utilize OS and hardware key/certificate management operations that may be natively available on the controller devices. Mobile app binaries and data can be encrypted, signed, and strongly obfuscated in local storage on controller devices. Biometric user authentication can be used on controller devices, such as smartphones.

Diabetes Management System Overview

Figure 9A:
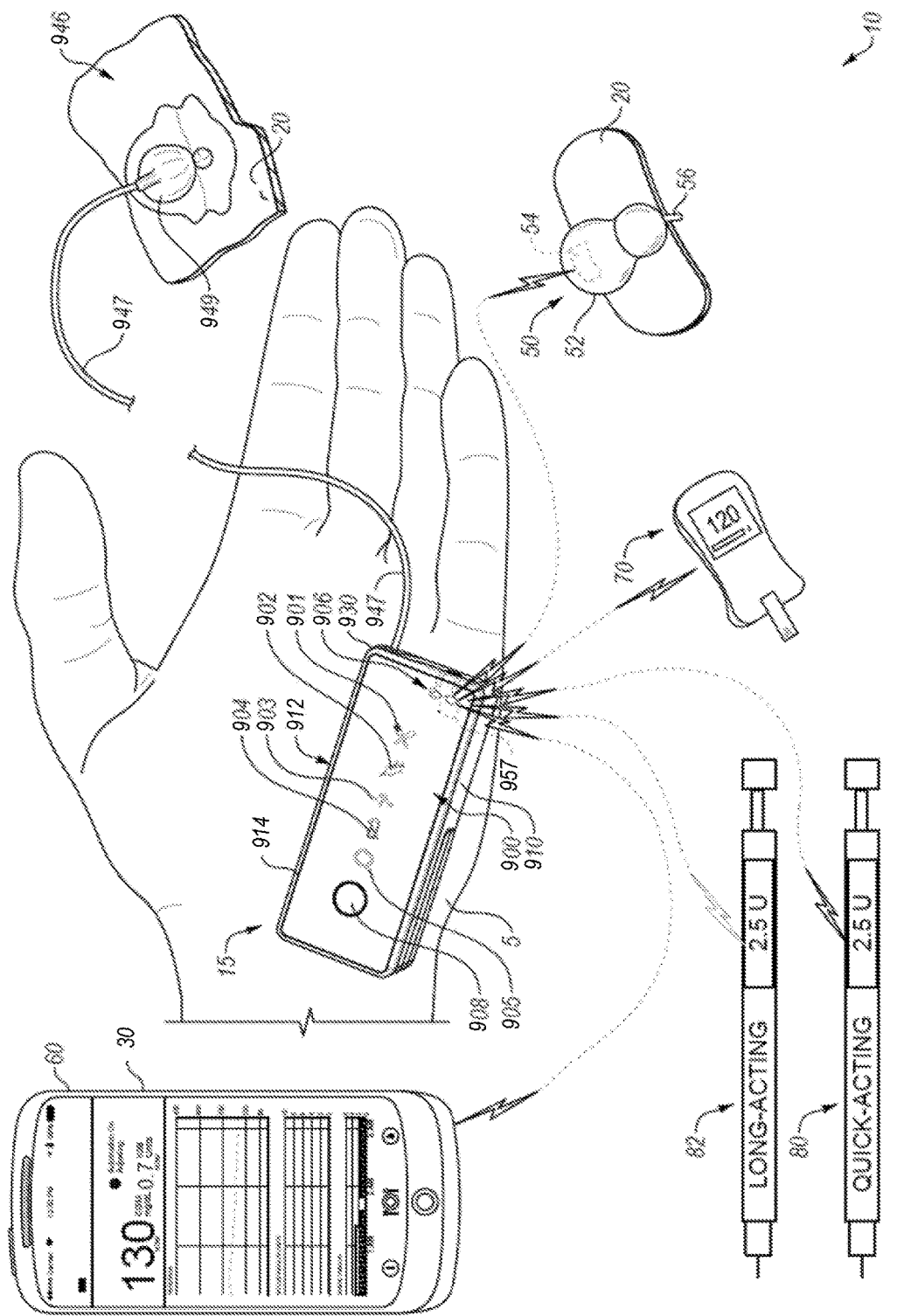
FIGS. 9A and 9B provide examples of a diabetes management system including an insulin pump assembly, a mobile computing device, a continuous glucose monitor, and a blood glucose monitor.
Figure 9B:
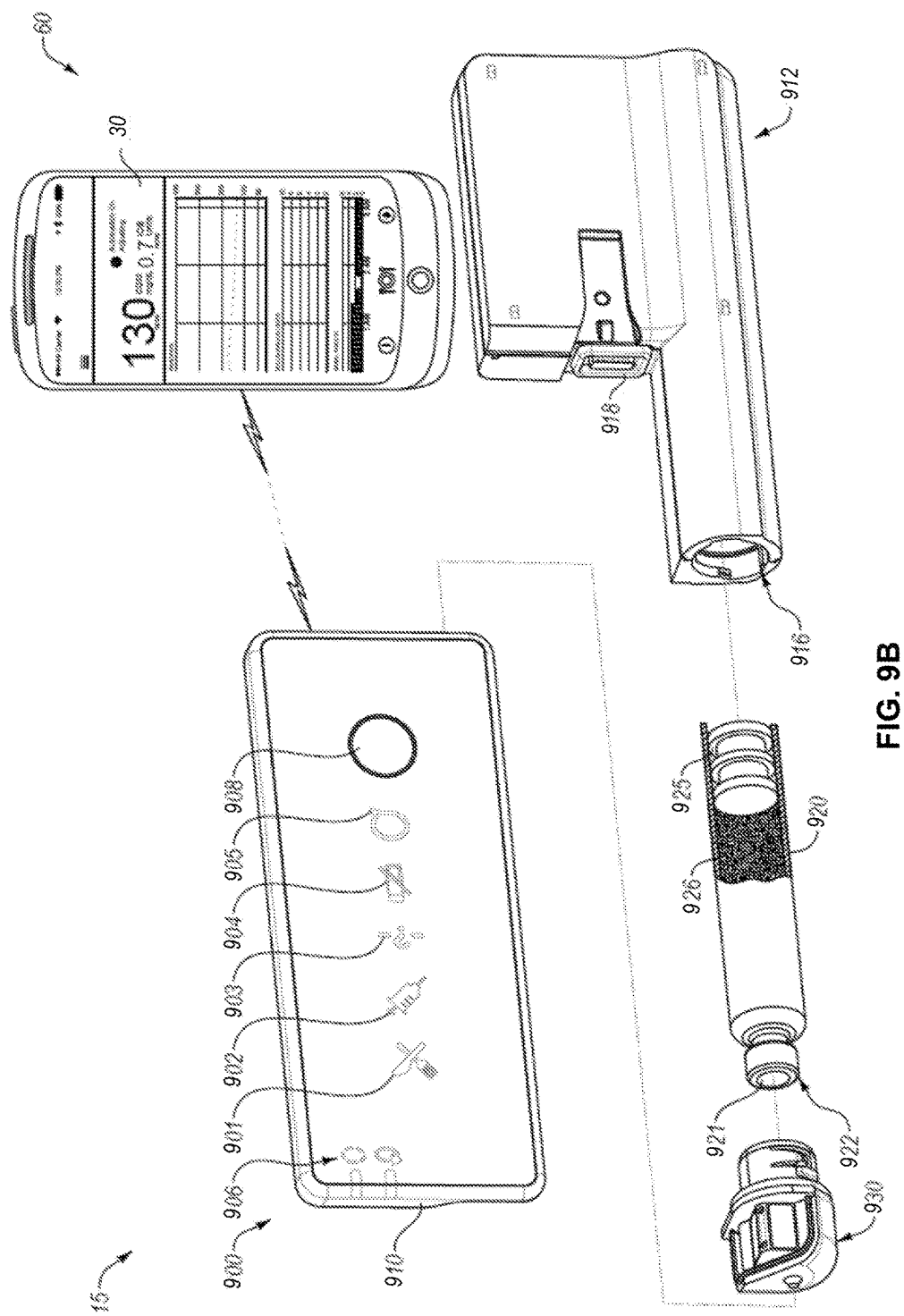
Figure 9C:
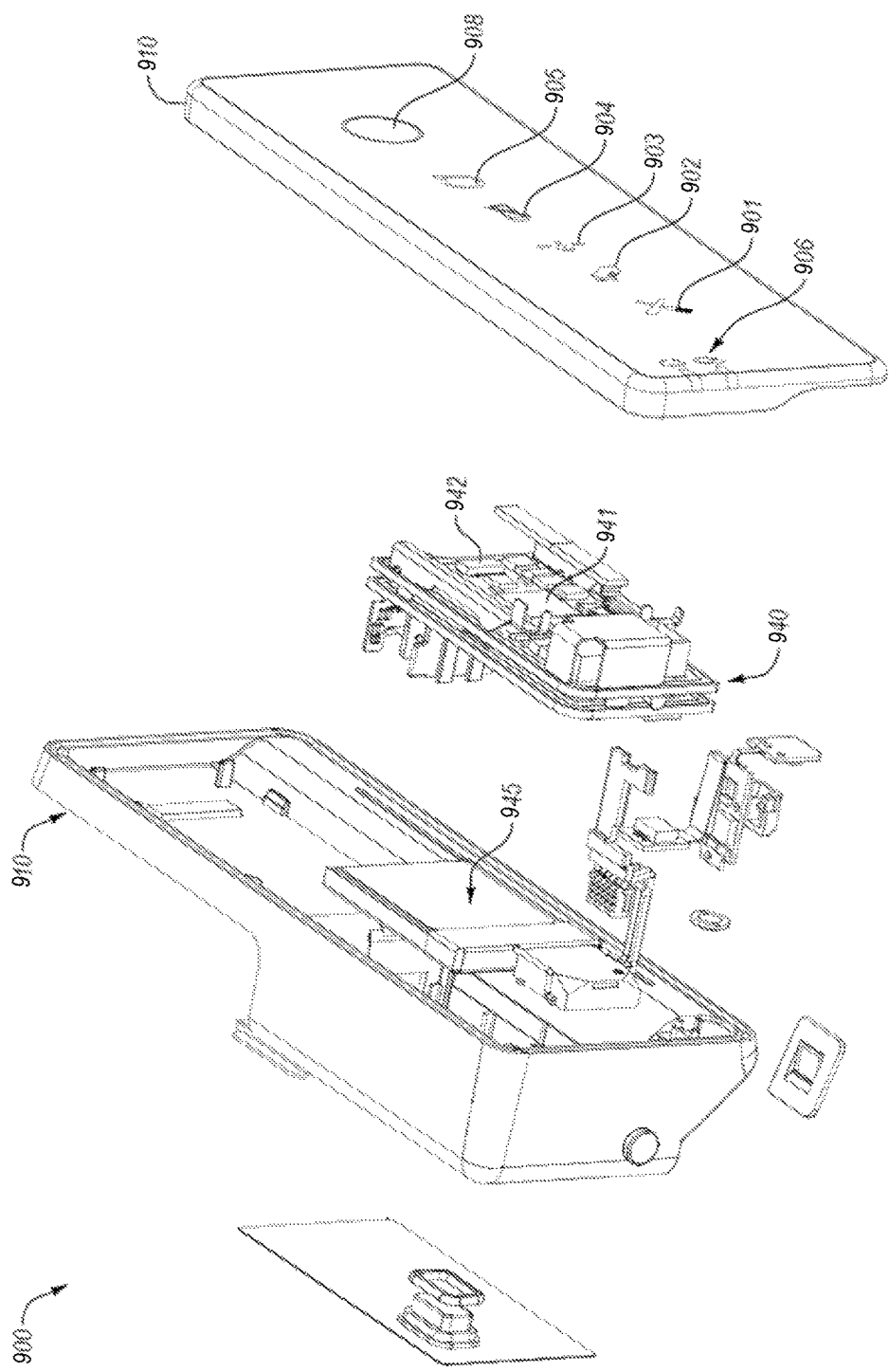
FIG. 9C depicts the details of an exemplary pump controller.

FIGS. 9A and 9B provide examples of a diabetes management system (DMS) 10 including an insulin pump assembly 15, a mobile computing device 60, a continuous glucose monitor 50, and a blood glucose monitor 70. FIG. 9C depicts the details of an exemplary pump controller, which can be used with DMS 10. The insulin pump assembly 15 is an example of a device, such as the devices 106, 906, and 306 described above. The mobile computing device 60 is an example of a controller, such as the controller 104, 904, and 304 described above.

Pump assembly 15 includes an infusion set 947 adapted to deliver insulin to an infusion site 946. In some cases, DMS 10 can include an insulin pen 80 or other insulin delivery device that can also be used to deliver insulin to a user. As shown, mobile computing device 60 is in wireless communication with insulin pump assembly 15. As shown, insulin pump assembly 15 is in wireless communication with continuous glucose monitor 50 and data from continuous glucose monitor 50 can be transferred to the mobile computing device 60 via insulin pump assembly 15. In some cases, continuous glucose monitor 50 can wirelessly communicate directly with mobile computing device 60. As shown, insulin pump assembly 15 is in wireless communication with blood glucose monitor 70 and data from blood glucose monitor 70 can be transferred to the mobile computing device 60 via insulin pump assembly 15. In some cases, blood glucose monitor 70 can wirelessly communicate directly with mobile computing device 60. In some cases, blood glucose monitor 70 can be unconnected from the system 10 and a user can manually input a blood glucose monitor reading into mobile computing device 60 (or into insulin pump assembly 15), either with or without a user prompt. In some cases, a blood glucose monitor 70 can be in wireless communication with the continuous glucose monitor 50.

As shown, controller 900 can include a limited user interface consisting of illuminable icons 901-906, which can provide indications regarding an operating mode of the pump assembly 15 and/or types of alarm or alert messages. In some cases, a user can view a more detailed message relating to an illuminated icon on the mobile computing device 60 via app 300. Controller 900 can additionally or alternatively issue audible notices (e.g., comprising audible words), audible tones, and/or haptic vibrations to indicate the presence of an alarm or alert. In some cases, alarm conditions can require more immediate user intervention, and can thus be presented with louder tones than alert conditions. In some cases, a button 908 can be present on controller 900 to permit user to check a status, using illuminable icons 901-906, and/or to snooze an alarm or alert. Although pump assembly 15 is depicted with a limited user interface intended to be used with a smartphone 60 and app 300 as the primary user interface, some implementations of the methods, devices, and systems provided herein can include a primary user interface directly on a pump assembly 15. In some cases, although depicted having a multi-part reusable/disposable construction, pump assemblies that are entirely disposable or entirely reusable and/or that have a unitary construction are also contemplated.

The features that are described herein can be extended to DMSs 10 that use alternative insulin delivery devices (e.g., insulin pens, patch pumps, syringes) and/or devices delivering other medicines (e.g., glucagon). In some cases, insulin pen 80 can be in wireless communication with mobile computing device 60. In some cases, user interfaces provided herein can be adapted to allow a user to manually input a bolus delivered using insulin pen 80. User interfaces described herein can also be used with any suitable insulin pump device, including patch pumps and/or other commercially available pumps. In some cases, an insulin pump assembly used in DSM 10 can have a unitary construction and have a reservoir adapted to be filled with insulin.

Exemplary Mobile Computing Device

Mobile computing device 60 can communicate with the controller device 900 through a wireless and/or wired connection with the controller device 900 (e.g., via a Bluetooth wireless communication connection in this particular implementations). In some cases, mobile computing device 60 communicates wirelessly with other elements of the system 10. Mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices able to detect a location of the mobile computing device. Sometimes location can be determined by detecting an available wifi network and/or other types of wireless networks/signals (e.g., detecting wireless beacon signals, BLUETOOTH signals, near field communication (NFC) signals). In some cases, location can be detected by using a global positioning system. In some cases, mobile computing device 60 can be used to transfer data from controller device 900 to the cloud. In some cases, the mobile computing device can be adapted to not share location information on the cloud or encrypt it so that it cannot be correlated to a physical address or latitude and longitude location. In some cases, the mobile computing device 60 provides a user interface (e.g., graphical user interface (GUI), speech-based user interface, motion-controlled user interface) through which users can provide information regarding maintenance activities and/or review upcoming scheduled maintenance tasks. Although mobile computing device 60 is depicted in FIG. 9A as including the primary user interface, with a limited user interface available on controller 900, in some cases methods, devices, and systems provided herein can have a primary user interface as part of pump assembly 15 and can operate with a mobile computing device 60 acting as a secondary user interface.

In implementations where the primary user interface is part of a mobile computing device, accessing the details of an alarm or an alert can require access to the paired mobile computing device. In some implementations of methods, systems, and devices provided herein, however, certain third-party devices can be authorized to allow connection to one or more peripheral devices of a diabetes management system (e.g., pump assembly 15, CGM 50, etc.) such that these authorized third-party devices (e.g., devices possessed by PWD designated assistance entities) can receive data from the peripheral devices, but not control the peripheral devices, even in the absence of an connected connected/operational paired mobile computing device. In some cases, the mobile computing device can be a mobile controlling device adapted to provide commands to the insulin pump assembly 15 (e.g., command the insulin pump assembly 15 to deliver a bolus).

Continuous Glucose Monitor

Continuous glucose monitor 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 90 of a user to make measurements indicative of characteristics of the user's blood (e.g., the user's blood glucose level or the like). In some cases, the sensor shaft 56 can measure glucose or another analyte in interstitial fluid or in another fluid and correlate that to blood glucose levels. In response to the measurements made by the sensor shaft 56, continuous glucose monitor 50 can employ the wireless communication device 54 to transmit data to a corresponding wireless communication device 957 housed in the pump system 15. In some cases, the monitoring device 50 may include a circuit that permits sensor signals (e.g., data from the sensor shaft 56) to be communicated to the communication device 54. The communication device 54 can transfer the collected data to the controller device 900 (e.g., by wireless communication to the communication device 957). Alternatively, the monitoring device 50 can employ other methods of obtaining information indicative of a user's blood characteristics and transferring that information to the controller device 900. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. Invasive methods involving optical means of measuring glucose could also be added. In yet another example, the monitoring device can include an optical detection instrument that is inserted through the skin for measuring the user's glucose level. Furthermore, it should be understood that in some alternative implementations, the monitoring device 50 can be in communication with the controller device 900 or another computing device via a wired connection.

Blood Glucose Meter

DMS 10 may optionally communicate with blood glucose meter 70 in addition to (or as an alternative to) continuous glucose meter 50. For example, one or more test strips (e.g., blood test strips) can be inserted into a strip reader portion of blood glucose meter 70 and then receive blood to be tested. In some cases, blood glucose meter 70 is configured to analyze the characteristics of the user's blood and to communicate (e.g., via a Bluetooth wireless communication connection) the information to the controller device 900. In some cases, a user can manually input a glucose meter reading. Blood glucose meter 70 can be manually operated by a user and may include an output subsystem (e.g., display, speaker) that can provide the user with blood glucose readings that can be subsequently entered into the controller or user interface (to collect the data from an unconnected BGM into the system). Blood glucose meter 70 may be configured to communicate data (e.g., blood glucose readings) obtained to the controller device 900 and/or other devices, such as the mobile computing device 60. Such communication can be over a wired and/or wireless connection, and the data can be used by the controller device 900 and/or the mobile computing device 60 to perform multiple delivery modes and/or a secondary feedback loop for the insulin delivery system 10.

External Insulin Delivery Devices

DMS 10 may include one or more external medication delivery devices 80 (e.g., syringe, an insulin pen, a smart syringe with device communication capabilities, or the like) through which additional medicine dosages (e.g., insulin, glucagon) can be manually administered to a user. In some cases, user interfaces provided herein allow users to input a medication, a dosage amount, and the timing so that a closed-loop control algorithm can account for the additional medication. In some cases, mobile computing device 60 can make a recommendation for an amount of insulin to be delivered using an external delivery device.

Pump Assembly

Referring again to FIG. 9A, pump assembly 15 can include pump device 912 configured to removably attach to the controller device 900 in a manner that provides a secure fitting, an overall compact size, and a reliable electrical connection. Additional details about the particularly depicted pump assembly 15 are described in more detail below in connection with FIGS. 9B and 9C.

Pump assembly 15 can be pocket-sized so that the pump device 912 and controller device 900 can be worn in the user's pocket or in another portion of the user's clothing. In some circumstances, the user may desire to wear the pump assembly 15 in a more discrete manner. Accordingly, the user can pass the tube 947 from the pocket, under the user's clothing, and to the infusion site where the adhesive patch can be positioned. As such, the pump assembly 15 can be used to deliver medicine to the tissues or vasculature of the user in a portable, concealable, and discrete manner.

In some cases, the pump assembly 15 can be configured to adhere to the user's skin directly at the location in which the skin is penetrated for medicine infusion. For example, a rear surface of the pump device 912 can include a skin adhesive patch so that the pump device 912 can be physically adhered to the skin of the user at a particular location. In these cases, the cap device 930 can have a configuration in which medicine passes directly from the cap device 930 into an infusion set 946 that is penetrated into the user's skin. In some examples, the user can temporarily detach the controller device 900 (while the pump device 912 remains adhered to the skin) so as to view and interact with the user interface 920.

Referring now to FIG. 9B, the pump device 912 in this example includes a housing structure 914 that defines a cavity 916 in which a fluid cartridge 920 can be received. The pump device 912 also can include a cap device 930 to retain the fluid cartridge 920 in the cavity 916 of the housing structure 914. The pump device 912 can include a drive system (e.g., including a battery powered actuator, a gear system, a drive rod, and other items that are not shown in FIG. 9A) that advances a plunger 925 in the fluid cartridge 920 so as to dispense fluid therefrom. In this example, the controller device 900 communicates with the pump device 912 to control the operation of the drive system. Optionally, the controller device 900 may be configured as a reusable component that provides electronics and a user interface to control the operation of the pump device 912. In such circumstances, the pump device 912 can be a disposable component that is disposed of after a single use. For example, the pump device 912 can be a "one time use" component that is thrown away after the fluid cartridge 920 therein is exhausted. Thereafter, the user can removably attach a new pump device (having a new fluid cartridge) to the reusable controller device 900 for the dispensation of fluid from a new fluid cartridge. Accordingly, the user is permitted to reuse the controller device 900 (which may include complex or valuable electronics, as well as a rechargeable battery) while disposing of the relatively low-cost pump device 912 after each use. Such a pump assembly 15 can provide enhanced user safety as a new pump device (and drive system therein) is employed with each new fluid cartridge. Additional and/or alternative implementations of the controller device 900 are also possible, including magnetic drive turbine (MDT) monolithic architecture pumps and/or patch pumps (e.g., an OMNIPOD).

The pump assembly 15 can be a medical infusion pump assembly that is configured to controllably dispense a medicine from the cartridge 920. As such, the fluid cartridge 920 can contain a medicine 926 to be infused into the tissue or vasculature of a targeted individual, such as a human or animal patient. For example, the pump device 912 can be adapted to receive a fluid cartridge 920 in the form of a carpule that is preloaded with insulin or another medicine for use in the treatment of Diabetes (e.g., Exenatide (BYETTA, BYDUREON) and Liraglutide (VICTOZA) SYMLIN, or others). Such a cartridge 920 may be supplied, for example, by Eli Lilly and Co. of Indianapolis, Ind. Other examples of medicines that can be contained in the fluid cartridge 920 include: pain relief drugs, hormone therapy, blood pressure treatments, anti-emetics, osteoporosis treatments, or other injectable medicines. The fluid cartridge 920 may have other configurations. For example, the fluid cartridge 920 may comprise a reservoir that is integral with the pump housing structure 914 (e.g., the fluid cartridge 920 can be defined by one or more walls of the pump housing structure 914 that surround a plunger to define a reservoir in which the medicine is injected or otherwise received).

In some cases, the pump device 912 can include one or more structures that interfere with the removal of the fluid cartridge 920 after the fluid cartridge 920 is inserted into the cavity 916. For example, the pump housing structure 914 can include one or more retainer wings (not shown) that at least partially extend into the cavity 916 to engage a portion of the fluid cartridge 920 when the fluid cartridge 920 is installed therein. Such a configuration may facilitate the "one-time-use" feature of the pump device 912. In some cases, the retainer wings can interfere with attempts to remove the fluid cartridge 920 from the pump device 912, thus ensuring that the pump device 912 will be discarded along with the fluid cartridge 920 after the fluid cartridge 920 is emptied, expired, or otherwise exhausted. In another example, the cap device 930 can be configured to irreversibly attach to the pump body 914 so as to cover the opening of the cavity 916. For example, a head structure of the cap device 930 can be configured to turn so as to threadably engage the cap device 930 with a mating structure along an inner wall of the cavity 916, but the head structure may prevent the cap device from turning in the reverse direction so as to disengage the threads. Accordingly, the pump device 912 can operate in a tamper-resistant and safe manner because the pump device 912 can be designed with a predetermined life expectancy (e.g., the "one-time-use" feature in which the pump device is discarded after the fluid cartridge 920 is emptied, expired, or otherwise exhausted).

Still referring to FIG. 9B, the controller device 900 can be removably attached to the pump device 912 so that the two components are mechanically mounted to one another in a fixed relationship. In some cases, such a mechanical mounting can also form an electrical connection between the removable controller device 900 and the pump device 912 (for example, at electrical connector 918 of the pump device 912). For example, the controller device 900 can be in electrical communication with a portion of the drive system (show shown) of the pump device 912. In some cases, the pump device 912 can include a drive system that causes controlled dispensation of the medicine or other fluid from the cartridge 920. In some cases, the drive system incrementally advances a piston rod (not shown) longitudinally into the cartridge 920 so that the fluid is forced out of an output end 922. A septum 921 at the output end 922 of the fluid cartridge 920 can be pierced to permit fluid outflow when the cap device 930 is connected to the pump housing structure 914. For example, the cap device 930 may include a penetration needle that punctures the septum 921 during attachment of the cap device 930 to the housing structure 914. Thus, when the pump device 912 and the controller device 900 are mechanically attached and thereby electrically connected, the controller device 900 communicates electronic control signals via a hardwired connection (e.g., electrical contacts along connector 918 or the like) to the drive system or other components of the pump device 912. In response to the electrical control signals from the controller device 900, the drive system of the pump device 912 causes medicine to incrementally dispense from the fluid cartridge 920. Power signals, such as signals from a battery (not shown) of the controller device 900 and from the power source (not shown) of the pump device 912, may also be passed between the controller device 900 and the pump device 912.

Cap device 930 of the pump device 912 can be configured to mate with an infusion set 946. In general, the infusion set 946 can be a tubing system that connects the pump assembly 15 to the tissue or vasculature of the user (e.g., to deliver medicine into the tissue or vasculature under the user's skin). The infusion set 946 can include a flexible tube 947 that extends from the pump device 912 to a subcutaneous cannula 949 that may be retained by a skin adhesive patch (not shown) that secures the subcutaneous cannula 949 to the infusion site. The skin adhesive patch can retain the infusion cannula 949 in fluid communication with the tissue or vasculature of the user so that the medicine dispensed through the tube 947 passes through the cannula 949 and into the user's body. The cap device 930 can provide fluid communication between the output end 922 (FIG. 5) of the fluid cartridge 920 and the tube 947 of the infusion set 946.

Referring now to FIG. 9C, the controller device 900 (shown in an exploded view) houses a number of components that can be reused with a series of successive pump devices 912. In particular, the controller device 900 can include control circuitry 940 and a rechargeable battery pack 945, each arranged in the controller housing 910. The rechargeable battery pack 945 may provide electrical energy to components of the control circuitry 940, other components of the controller device (e.g., the display device 922 and other user interface components, sensors, or the like), or to components of the pump device 912. The control circuitry 940 may be configured to communicate control or power signals to the drive system of the pump device 912, or to receive power or feedback signals from the pump device 912.

The control circuitry 940 of the controller device 900 can include one or more microprocessors 941 configured to execute computer-readable instructions stored on one or more memory devices 942 so as to achieve any of the control operations described herein. At least one memory device 942 of the control circuitry may be configured to store a number of user-specific dosage parameters. Various user-specific dosage parameters can be automatically determined and/or updated by control operations implemented by the control circuitry 940 of the controller device 900. Additionally, the control circuitry 940 can cause the controller device 900 to periodically communicate the user-specific dosage parameters to the mobile computing device 60 for future use during operations by the mobile computing device 60 or for subsequent communication to cloud-based computer network.

In some cases, the control circuitry 940 can receive input data or other information from the mobile computing device 60 (e.g., via user input at the mobile computing device 60) and thereby cause the controller device 900 to output information to the mobile computing device 60 for display on the screen of the mobile computing device 60, such as settings and data (e.g., review data that shows the medicine dispensing rate, the total amount of medicine dispensed in a given time period, the amount of medicine scheduled to be dispensed at a particular time or date, the approximate amount of medicine remaining the cartridge 920, the amount of battery life remaining, or the like). The control circuitry 940 can be programmable to cause the control circuitry 940 to change any one of a number of settings or modes of operation for the insulin delivery system 10. In some cases, the control circuitry 940 can include a cable connector (e.g., a USB connection port or another data cable port) that is accessible on an external portion of the controller housing 910. As such, a cable can be connected to the control circuitry 940 to upload or download data or program settings to the control circuitry.

Out-of-Band Controller App Verification

Figure 10:
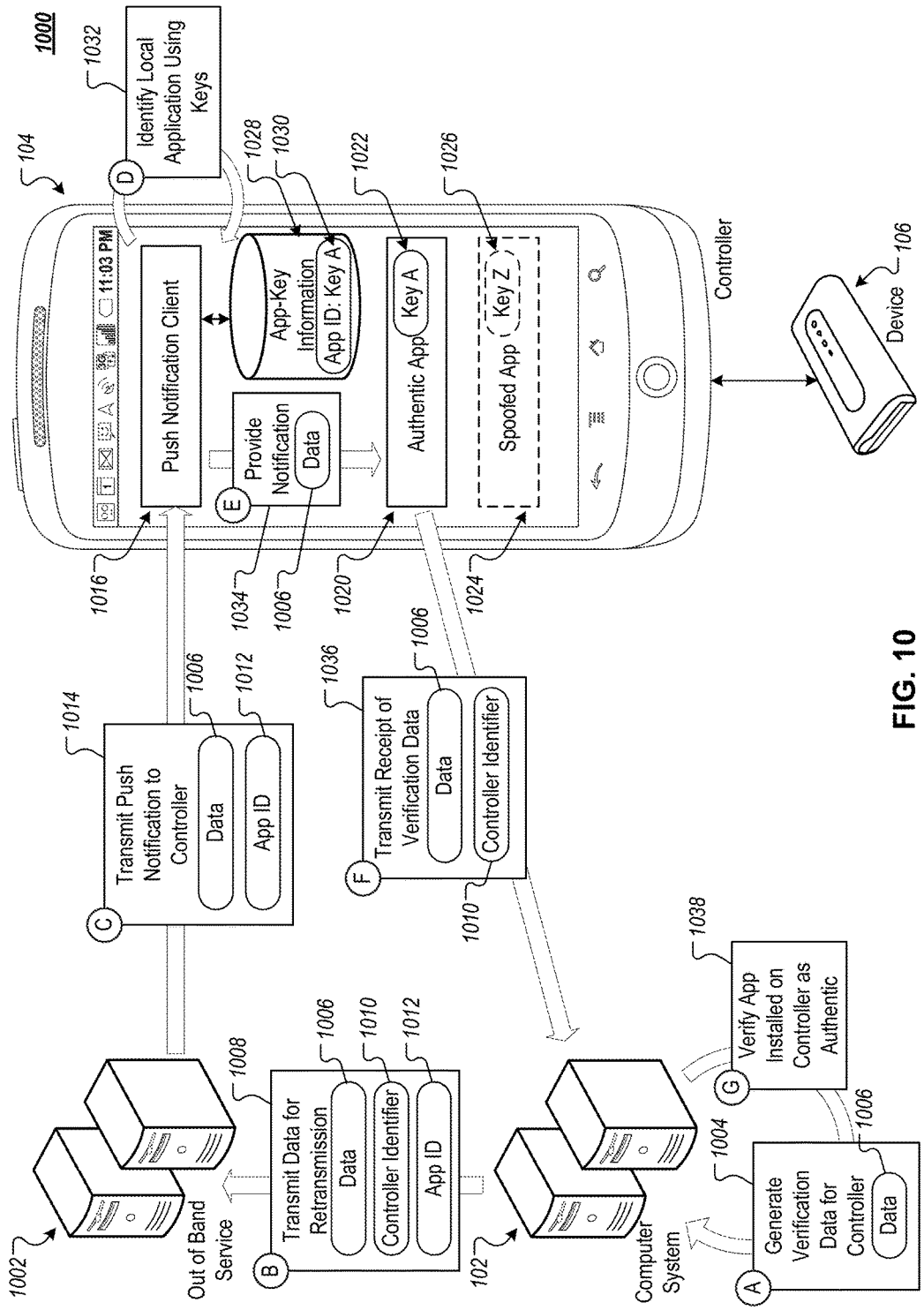
FIG. 10 is a conceptual diagram of an example system for providing out-of-band verification of an application running on a controller.

FIG. 10 is a conceptual diagram of an example system 1000 for providing out-of-band verification of an application running (e.g., mobile app) running on the controller 104. The system 1000 can provide a technique through which the authenticity of the mobile app that is running on the controller to, for example, control operation of the device 106 and to interface with the computer system 102 can be verified through a third party channel. For example, it is possible that a malicious application could be coded and loaded onto the controller 104 to mimic the in-band interactions with the computer system 102 and the device 106 such that the computer system 102 and the device 106 may not be able to readily detect that the application is not authentic, but instead is malicious third party software. Such malicious third party software, however, could pose security risks, particularly around user privacy and safe/secure operation of the device 106. The system 1000 permits for out-of-band systems and channels of communication-meaning communication channels different from those between the computer system 102 and the controller 104 and between the controller 104 and the device 106—to verify the authenticity of the mobile app running on the controller 104, which can be used to thwart any attempts to run third party software that would otherwise mimic the actual application on the controller 104.

To do this, the system 1000 includes an out-of-band service 1002 (e.g., computer system and services, cloud based computer system and services) that is configured to transmit notifications that can only be relayed to an authentic application running on the controller 104, and would not otherwise be relayed to an inauthentic/spoofed application (e.g., malicious third party software). The computer system 102 can be programmed to generate a secret (e.g., random data value that is not shared with the controller 104 via in-band communication) that will be transmitted in the payload of the out-of-band notification that is provided to the controller 104, and authentic mobile apps can be programmed to retransmit the secret back to the computer system 102 once received via the out-of-band communication to verify that they are authentic. The out-of-band service 1002 can be a service, for example, that is associated with the distribution, installation, and notifications that are provided to mobile apps, such as APPLE'S APP STORE and the GOOGLE PLAY STORE. Other types of out-of-band services 1002 are also possible, such as carrier network services, mobile data network services, and/or other services.

As an example technique for out-of-band application authentication, the computer system 102 generates verification data 1006 that is intended to be transmitted to the controller 104 to verify the authenticity of the mobile application installed and running thereon, as indicated by step A (1004). For example, the computer system 102 can generate a random value (e.g., random integer, random string of characters) specifically for the controller 104 that the computer system 102 stores in association with the controller 104 (e.g., stores in association with a controller identifier, such as an account associated with the controller 104, a phone number for the controller 104, identifier for the application installed on the controller 104), and which can be used to verify the application on the controller 104.

As indicated by step B (1008), the computer system 102 transmits the data 1006 to the out-of-band service 1002 for retransmission to the controller 104. The request for retransmission of the data 1006 to the controller 104 can include, for example, a controller identifier 1010 that the out-of-band service 1002 can use to identify and deliver the data 1006 to the controller 104. The request for retransmission can also include an application identifier 1012 that can uniquely identify the application (from among multiple applications that are serviced by the out-of-band service 1002) to which the data 1006 is to be delivered on the controller 104. For example, the application identifier 1012 can be a unique identifier that the out-of-band service 1002 associates with the application serviced by the computer system 102 (e.g., the computer system 102 can provide mobile app services for the application identified by the app ID 1012) and uses to differentiate between different applications. The app ID 1012 can also be used by the controller 104 to identify a corresponding local instance of the application installed on the controller 104, so as to ensure that notifications and other messaging provided by the out-of-band service 1002 are routed to the appropriate application locally installed on the controller 104.

As indicated by step C (1014), the out-of-band service 1002 can transmit a push notification (example of a message/data transmission to provide out-of-band information to authentic applications on the controller 104) to the controller 104 (using the controller identifier 1010) with the data 1006 in the payload and with the app ID 1012. The controller 104 has a push notification client 1016, which may be part of the operating system on the controller 104, that is configured to receive all push notifications delivered to the controller 104. The push notification client 1016 can use a local repository 1028 of information that correlates local application instances on the controller 104 with applications managed by the out-of-band service 1002. The local repository 1028 can serve as an authentication ledger for applications installed on the controller 104 to ensure that notifications for a particular application are delivered only to authentic local instances of the application on the controller 104. For example, the local repository 1028 can provide a secure keychain of keys for local application instances, where the keys uniquely identify local application instances installed on the controller 104. For example, the repository 1028 includes information 1030 indicating that the local instance of the application (identified by the app ID 1012) on the controller 104 is identified by example key A (e.g., unique identifier on the controller 104).

As indicated by step D (1032), the push notification client 1016 can receive the push notification and use the app ID 1012 and the local repository 1028 to identify the authentic local instance of the application (identified by the app ID 1012) to receive the notification. In this example, the controller 104 includes an authentic app 1020 that includes, is identified by, or associated with the key A 1022. In such an instance, the push notification client 1016 uses the information 1030 to determine that the authentic local instance of the application to receive the notification is the application 1020 identified by the key A 122, and can provide the notification with the data 1006 to the application 1020, as indicated by step E (134). Accordingly, the out-of-band service 1002 can be used to transmit a secret generated by the computer system 102 out of band to the authentic app 1020. As indicated by step F (1036), the authentic application 1020 can be programmed to automatically retransmit the data 1006 (secret) back to the computer system 102 along with the controller identifier 1010, which the computer system 102 can use to verify that the application installed and running on the controller 104 is authentic, as indicated by step G (1038). For example, if the data 1006 received from the controller 104 matches that data stored in association with the controller identifier 1010, then the computer system 102 can determine that the application installed on the controller is authentic 104.

In contrast, if a spoofed application 1024 were to be installed and running on the controller 104 instead of the authentic app 1020, the push notification client 1016 would not provide the notification or the data 1006 to the spoofed app 1024 based on the key 1026 for the spoofed app 1024 not matching the key for the app ID 1012 in the local repository 1028. In such an instance, the data 1006 would not be retransmitted back to the computer system 102 in association with the controller identifier 1010 (step F, 1036 would not be performed). The computer system 102 can be programmed to monitor for this retransmission and, if the retransmission has not been received within a threshold period of time (e.g., 30 seconds, 1 minute, 5 minutes, 1 hour, 1 day, 1 week) since the data 1006 was originally transmitted to the out-of-band service 1002 (step B, 1008), the controller 102 can be programmed to automatically determine that the controller 104 is running a spoofed/inauthentic application and can escalate the situation to the patient/user of the controller 104, medical professionals (e.g., physician, nurse, healthcare network), and/or other services that can take proactive action to remove the spoofed app 1024 from the controller 104.

The out-of-band application authentication features described with regard to system 1000 and FIG. 10 can be used alone or combined with any of the other features described above, such as the features described with regard to FIGS. 1-9.

Figure 11:
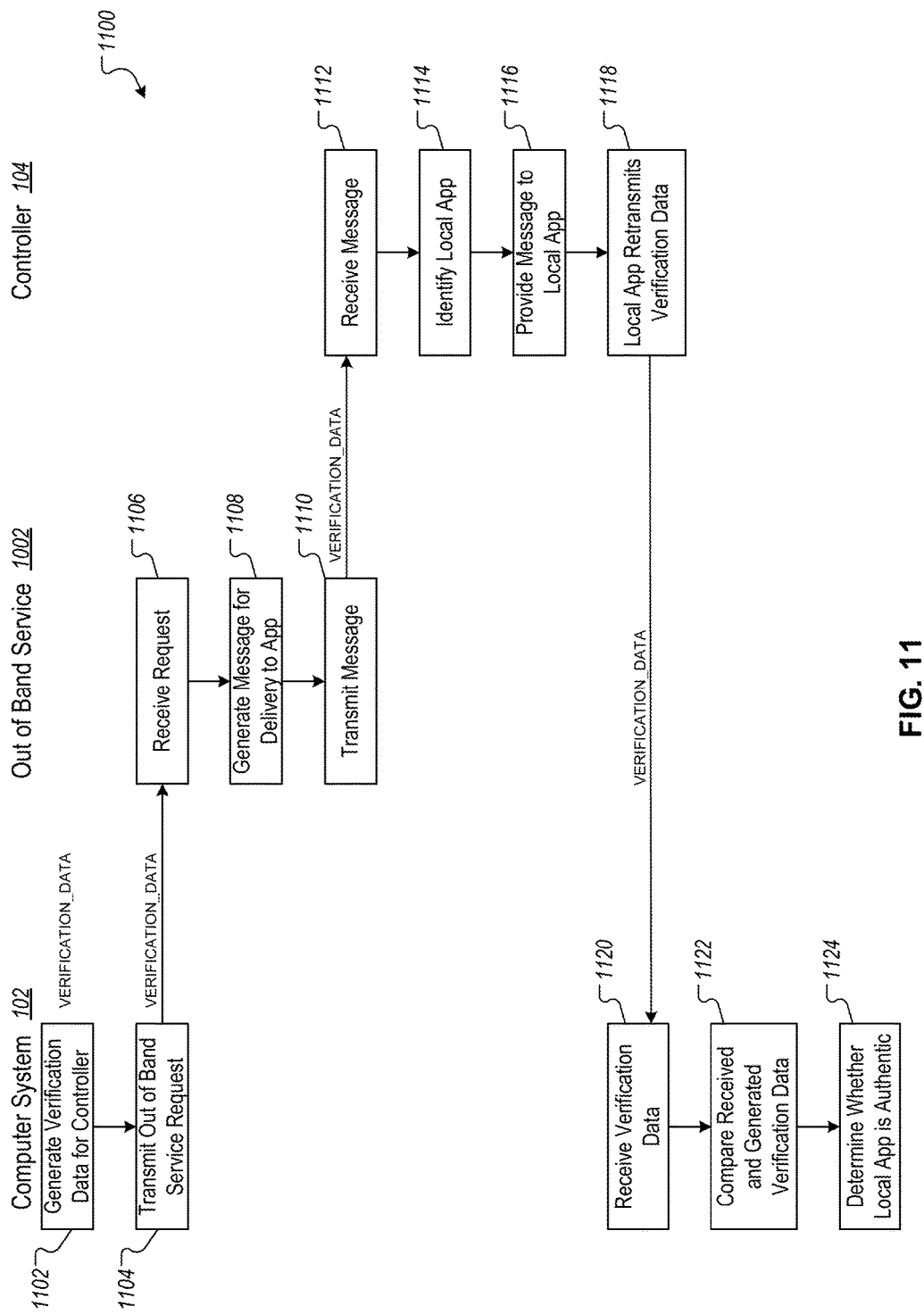
FIG. 11 is a flowchart of an example technique for performing out-of-band application authentication between a computer system, an out-of-band service, and a controller.

FIG. 11 is a flow chart of an example technique 1100 for performing out-of-band application authentication between a computer system 102, an out-of-band service 1002, and a controller 104. The example technique 1100 can be used alone or in combination with one or more of the example techniques 300, 400, 500, 600, 700, 800, and 850 described above.

The computer system 102 generated verification data (VERIFICATION_DATA) for the controller 104 (1102), as described above with regard to step A, 1004. The computer system 102 can transmit an out-of-band service request with the verification data to the out-of-band service 1002 that is associated with the controller 104 (1104), which the out-of-band service 1002 can receive (1106) and can use to generate a message for out-of-band delivery to an authentic application installed/running on the controller 104 (1108). For example, the message can be a push notification that identifies the application identifier for the local instance of the application running on the controller 104 and that includes the verification data in the payload of the notification. The push notification can additionally include one or more flags, codes, tags, or instructions that indicate that the verification data is being provided for out-of-band verification, which can prompt an authentic application on the controller 104 to automatically transmit the verification data back to the computer system 102. Other types of messages are also possible, such as email and/or other messaging mediums (e.g., social network messaging) that may be automatically routed to appropriate applications on the controller 104 via out of band communication channels. Once the message has been generated, the message can be transmitted with the verification data to the controller 104 (1110).

The controller 104 can receive the message (1112) and can use the information in the message to identify a local application instance to receive the message (1114). For example, as discussed above with regard to step D, 1032, a local repository can be used to identify an authentic instance of the application on the controller 104. Other techniques are also possible, such as identifying applications with particular signatures and/or other unique/quasi-unique identifiers or features. Once the local application has been identified via out-of-channel communication, the message can be provided to the local application (1116), which can be automatically programmed to retransmit the verification data back to the computer system 102 (1118).

The computer system 102 can receive the verification data from the controller 104 (1120) and can compare it to the generated verification data (1122). If the received and the generated verification data match and/or pass other types of comparisons/analyses, then the computer system 102 can determine that the local app is authentic (1124). However, if the computer system 102 receives verification data from the controller 104 that does not match and/or pass other types of comparisons/analyses, then the computer system 102 can determine that the application installed on the controller 104 is not authentic. Similarly, if the computer system 102 does not receive a response from the controller 104 within a threshold period of time since transmitting the out of band service request (1104), then the computer system 102 can determine that the application installed on the controller 102 is not authentic. As described with regard to FIG. 10, such determinations that the application on the controller 104 is not authentic can result in one or more notifications being sent out to the user/patient of the controller 104 and/or others associated with the user/patient (e.g., physician, emergency contact, employer, device manufacturer) to assist with remedying the situation.

Figure 12:
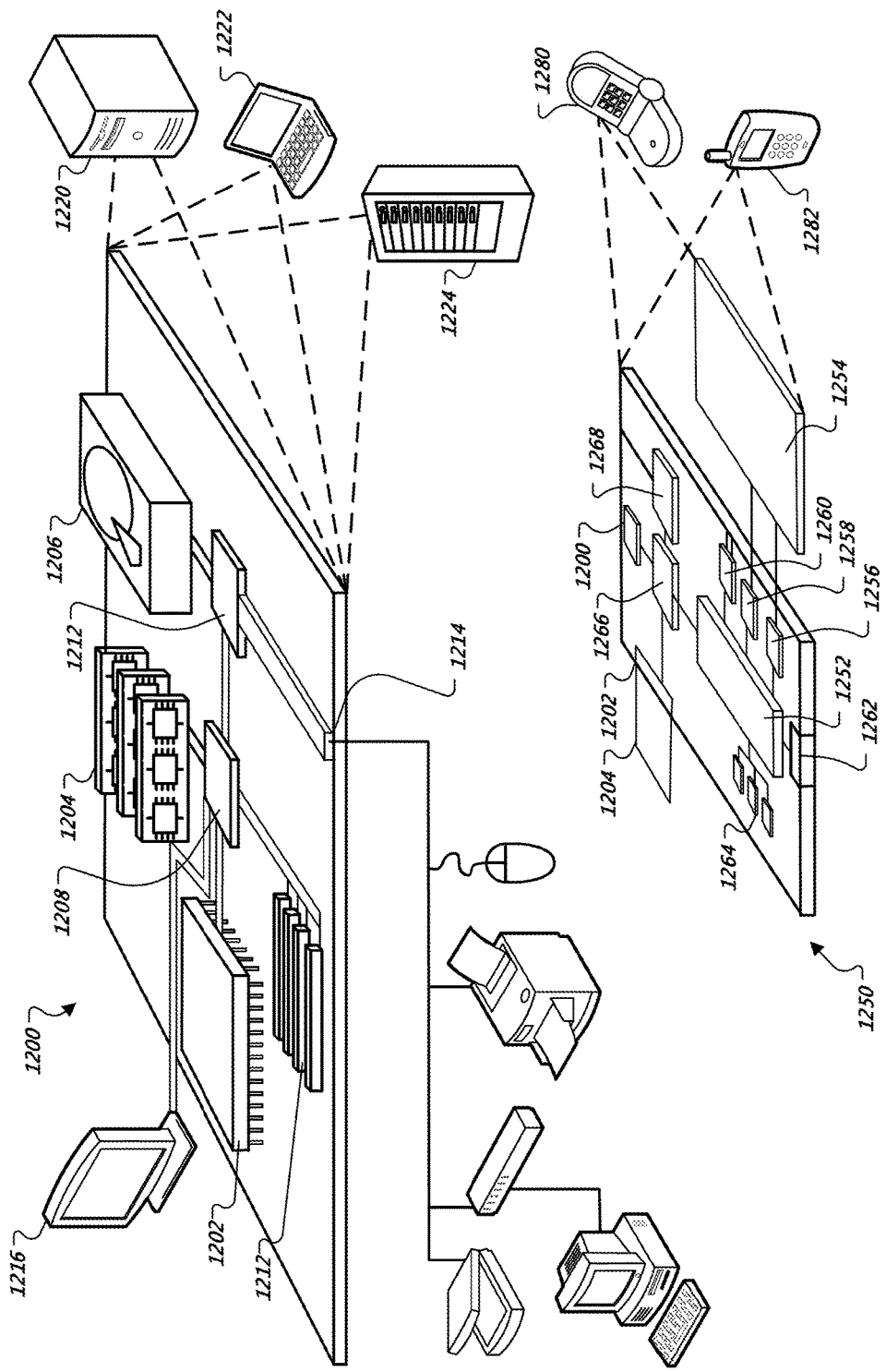
FIG. 12 is a block diagram of example computing devices that may be used to implement the systems and methods described in this document.

FIG. 12 is a block diagram of computing devices 1200, 1250 that may be used to implement the systems and methods described in this document, as either a client or as a server or plurality of servers. Computing device 1200 is intended to represent various forms of digital computers, such as laptops, desktops, workstations, personal digital assistants, servers, blade servers, mainframes, and other appropriate computers. Computing device 1250 is intended to represent various forms of mobile devices, such as personal digital assistants, cellular telephones, smartphones, and other similar computing devices. Additionally computing device 1200 or 1250 can include Universal Serial Bus (USB) flash drives. The USB flash drives may store operating systems and other applications. The USB flash drives can include input/output components, such as a wireless transmitter or USB connector that may be inserted into a USB port of another computing device. The components shown here, their connections and relationships, and their functions, are meant to be exemplary only, and are not meant to limit implementations described and/or claimed in this document.

Computing device 1200 includes a processor 1202, memory 1204, a storage device 1206, a high-speed interface 1208 connecting to memory 1204 and high-speed expansion ports 1210, and a low speed interface 1212 connecting to low speed bus 1214 and storage device 1206. Each of the components 1202, 1204, 1206, 1208, 1210, and 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as display 1216 coupled to high speed interface 1208. In other implementations, multiple processors and/or multiple buses may be used, as appropriate, along with multiple memories and types of memory. Also, multiple computing devices 1200 may be connected, with each device providing portions of the necessary operations (e.g., as a server bank, a group of blade servers, or a multi-processor system).

The memory 1204 stores information within the computing device 1200. In one implementation, the memory 1204 is a volatile memory unit or units. In another implementation, the memory 1204 is a non-volatile memory unit or units. The memory 1204 may also be another form of computer-readable medium, such as a magnetic or optical disk.

The storage device 1206 is capable of providing mass storage for the computing device 1200. In one implementation, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1204, the storage device 1206, or memory on processor 1202.

The high speed controller 1208 manages bandwidth-intensive operations for the computing device 1200, while the low speed controller 1212 manages lower bandwidth-intensive operations. Such allocation of functions is exemplary only. In one implementation, the high-speed controller 1208 is coupled to memory 1204, display 1216 (e.g., through a graphics processor or accelerator), and to high-speed expansion ports 1210, which may accept various expansion cards (not shown). In the implementation, low-speed controller 1212 is coupled to storage device 1206 and low-speed expansion port 1214. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. It may also be implemented as part of a rack server system 1224. In addition, it may be implemented in a personal computer such as a laptop computer 1222. Alternatively, components from computing device 1200 may be combined with other components in a mobile device (not shown), such as device 1250. Each of such devices may contain one or more of computing device 1200, 1250, and an entire system may be made up of multiple computing devices 1200, 1250 communicating with each other.

Computing device 1250 includes a processor 1252, memory 1264, an input/output device such as a display 1254, a communication interface 1266, and a transceiver 1268, among other components. The device 1250 may also be provided with a storage device, such as a microdrive or other device, to provide additional storage. Each of the components 1250, 1252, 1264, 1254, 1266, and 1268, are interconnected using various buses, and several of the components may be mounted on a common motherboard or in other manners as appropriate.

The processor 1252 can execute instructions within the computing device 1250, including instructions stored in the memory 1264. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 1250, such as control of user interfaces, applications run by device 1250, and wireless communication by device 1250.

Processor 1252 may communicate with a user through control interface 1258 and display interface 1256 coupled to a display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may be provided in communication with processor 1252, so as to enable near area communication of device 1250 with other devices. External interface 1262 may provide, for example, for wired communication in some implementations, or for wireless communication in other implementations, and multiple interfaces may also be used.

The memory 1264 stores information within the computing device 1250. The memory 1264 can be implemented as one or more of a computer-readable medium or media, a volatile memory unit or units, or a non-volatile memory unit or units. Expansion memory 1274 may also be provided and connected to device 1250 through expansion interface 1272, which may include, for example, a SIMM (Single In Line Memory Module) card interface. Such expansion memory 1274 may provide extra storage space for device 1250, or may also store applications or other information for device 1250. Specifically, expansion memory 1274 may include instructions to carry out or supplement the processes described above, and may include secure information also. Thus, for example, expansion memory 1274 may be provided as a security module for device 1250, and may be programmed with instructions that permit secure use of device 1250. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1264, expansion memory 1274, or memory on processor 1252 that may be received, for example, over transceiver 1268 or external interface 1262.

Device 1250 may communicate wirelessly through communication interface 1266, which may include digital signal processing circuitry where necessary. Communication interface 1266 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1268. In addition, short-range communication may occur, such as using a Bluetooth, WiFi, or other such transceiver (not shown). In addition, GPS (Global Positioning System) receiver module 1270 may provide additional navigation- and location-related wireless data to device 1250, which may be used as appropriate by applications running on device 1250.

Device 1250 may also communicate audibly using audio codec 1260, which may receive spoken information from a user and convert it to usable digital information. Audio codec 1260 may likewise generate audible sound for a user, such as through a speaker, e.g., in a handset of device 1250. Such sound may include sound from voice telephone calls, may include recorded sound (e.g., voice messages, music files, etc.) and may also include sound generated by applications operating on device 1250.

The computing device 1250 may be implemented in a number of different forms, as shown in the figure. For example, it may be implemented as a cellular telephone 1280. It may also be implemented as part of a smartphone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front-end component (e.g., a client computer having a graphical user interface or a Web browser through which a user can interact with an implementation of the systems and techniques described here), or any combination of such back-end, middleware, or front-end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. Moreover, other mechanisms for performing the systems and methods described in this document may be used. In addition, the logic flows depicted in the figures do not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:

1. A computer-implemented method of establishing a secure wireless communication connection between an insulin pump device and a mobile computing device using a remote server system, the method comprising:
   receiving, at the mobile computing device, a device identifier for at least the insulin pump device, wherein the insulin pump device includes an insulin reservoir to store insulin to be administered to a user, a pump assembly to deliver insulin from the insulin reservoir to the user, and a controller to control operation of the pump assembly according, at least in part, to commands provided to the insulin pump by the mobile computing device;
   obtaining, by the mobile computing device, device information for the insulin pump device from the remote server system using the device identifier;
   establishing, by the mobile computing device, a secure wireless connection with the insulin pump device using, at least in part, the device identifier;
   authenticating, by the mobile computing device, the insulin pump device based on asymmetric key verification using a public key of an asymmetric key pair, the authentication including:
      sending a first challenge to the insulin pump device that includes a first value;
      determining a first response based on the first value and a shared secret;
      receiving the first response from the insulin pump device, wherein the insulin pump device is authenticated based on receipt of the first response;
      receiving, by the mobile computing device, a second challenge from the insulin pump device that includes a second value;
      determining, by the mobile computing device, a second response based on the second value and the shared secret;
      sending, by the mobile computing device, the second response to the insulin pump device; and
   securely communicating, by the mobile computing device and in response to authenticating the insulin pump device, information with the insulin pump device.

2. The computer-implemented method of claim 1, wherein receiving the device identifier comprises:
   optically scanning, using a digital camera that is embedded within or otherwise in communication with the mobile computing device, a barcode on one or more surfaces of the insulin pump device; and
   identifying the device identifier based on the optical scanning of the barcode.

3. The computer-implemented method of claim 1, wherein receiving the device identifier comprises:
   receiving, through a user interface of the mobile computing device, user input that identifies at least a portion of the device identifier.

4. The computer-implemented method of claim 1, wherein the device identifier comprises a serial number for the insulin pump device.

5. The computer-implemented method of claim 1, wherein the secure wireless connection comprises a BLUETOOTH connection.

6. The computer-implemented method of claim 1, wherein the insulin pump further includes a crypto processor that is configured to encrypt and decrypt information securely communicated with the mobile computing device.

7. The computer-implemented method of claim 1, wherein the communication between the mobile computing device and the insulin pump device is encrypted using symmetric key encryption.

8. The computer-implemented method of claim 7, wherein the symmetric key encryption comprises AES-CBC symmetric key encryption.

9. The computer-implemented method of claim 1, wherein the mobile computing device comprises a smartphone.

10. Computer readable media storing instructions to cause an electronic processor of a mobile computing device to perform operations for establishing a secure wireless communication connection between an insulin pump device and the mobile computing device using a remote server system, the operations comprising:
   receiving, at the mobile computing device, a device identifier for at least the insulin pump device, wherein the insulin pump device includes an insulin reservoir to store insulin to be administered to a user, a pump assembly to deliver insulin from the insulin reservoir to the user, and a controller to control operation of the pump assembly according, at least in part, to commands provided to the insulin pump by the mobile computing device;
   obtaining, by the mobile computing device, device information for the insulin pump device from the remote server system using the device identifier;
   establishing, by the mobile computing device, a secure wireless connection with the insulin pump device using, at least in part, the device identifier;
   authenticating, by the mobile computing device, the insulin pump device based on asymmetric key verification using a public key of an asymmetric key pair, the authentication including:
      sending a first challenge to the insulin pump device that includes a first value;
      determining a first response based on the first value and a shared secret;

receiving the first response from the insulin pump device, wherein the insulin pump device is authenticated based on receipt of the first response;

receiving, by the mobile computing device, a second challenge from the insulin pump device that includes a second value;

determining, by the mobile computing device, a second response based on the second value and the shared secret;

sending, by the mobile computing device, the second response to the insulin pump device; and securely communicating, by the mobile computing device and in response to authenticating the insulin pump device, information with the insulin pump device.

11. The computer readable media of claim 10, wherein receiving the device identifier comprises:

optically scanning, using a digital camera that is embedded within or otherwise in communication with the mobile computing device, a barcode on one or more surfaces of the insulin pump device; and identifying the device identifier based on the optical scanning of the barcode.

12. The computer readable media of claim 10, wherein receiving the device identifier comprises:

receiving, through a user interface of the mobile computing device, user input that identifies at least a portion of the device identifier.

13. The computer readable media of claim 10, wherein the device identifier comprises a serial number for the insulin pump device.

14. The computer readable media of claim 10, wherein the secure wireless connection comprises a BLUETOOTH connection.

15. The computer readable media of claim 10, wherein the insulin pump further includes a crypto processor that is configured to encrypt and decrypt information securely communicated with the mobile computing device.

16. The computer readable media of claim 10, wherein the communication between the mobile computing device and the insulin pump device is encrypted using symmetric key encryption.

17. The computer readable media of claim 16, wherein the symmetric key encryption comprises AES-CBC symmetric key encryption.

18. The computer readable media of claim 10, wherein the mobile computing device comprises a smartphone.

19. A method for authenticating a mobile application installed on a diabetes management controller, the method comprising:

generating, by a diabetes management computer system, a secret value to be used to verify authenticity of the mobile application installed on the diabetes management controller, wherein the diabetes management controller comprises a mobile computing device that interfaces with an insulin pump and the diabetes management computer system over in-band communication channels to control operation of the insulin pump;

transmitting, by the diabetes management computer system, a request to an out-of-band service to provide the secret value to the mobile application via an out-of-band communication channel that is different from the in-band communication channels, wherein the transmitting causes:

(i) the secret value to be transmitted to the diabetes management controller via the out-of-band communication channel, (ii) the diabetes management controller to provide the secret value to an authentic instance of the mobile application installed on the diabetes management controller, and (iii) the authentic instance of the mobile application on the diabetes management controller to automatically retransmit the secret value to the diabetes management computer system;

receiving, at the diabetes management computer system, verification value from the diabetes management controller;

comparing, by the diabetes management computer system, the verification value to the secret value; and determining, by the diabetes management computer system, that the instance of the mobile application installed on the diabetes management controller is authentic based, at least in part, on the comparison of the verification value with the secret value.

20. The method of claim 19, further comprising:

automatically initiating a timer on the diabetes management computer system after transmitting the request to the out-of-band service, the timer being programmed to expire if the verification value is not received within a threshold period of time since initiating the timer, wherein expiration of the timer indicates that the mobile application installed on the diabetes management controller is not authentic.

* * * * *